(12) United States Patent
Armstrong et al.

(10) Patent No.: US 12,018,091 B2
(45) Date of Patent: Jun. 25, 2024

(54) HIGH-CONCENTRATION MONOCLONAL ANTIBODY FORMULATIONS

(71) Applicant: Genentech, Inc., South San Francisco, CA (US)

(72) Inventors: Nicholas J. Armstrong, South San Francisco, CA (US); Mayumi N. Bowen, South San Francisco, CA (US); Yuh-Fun Maa, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 334 days.

(21) Appl. No.: 17/083,163

(22) Filed: Oct. 28, 2020

(65) Prior Publication Data

US 2021/0292435 A1 Sep. 23, 2021

Related U.S. Application Data

(63) Continuation of application No. 16/383,270, filed on Apr. 12, 2019, now abandoned, which is a continuation of application No. 14/752,670, filed on Jun. 26, 2015, now abandoned, which is a continuation of application No. 13/896,622, filed on May 17, 2013, now abandoned.

(60) Provisional application No. 61/649,146, filed on May 18, 2012.

(51) Int. Cl.
| | |
|---|---|
| *C07K 16/40* | (2006.01) |
| *A61K 9/00* | (2006.01) |
| *A61K 9/10* | (2006.01) |
| *A61K 9/16* | (2006.01) |
| *A61K 39/395* | (2006.01) |
| *C07K 16/22* | (2006.01) |
| *C07K 16/28* | (2006.01) |
| *C07K 16/32* | (2006.01) |

(52) U.S. Cl.
CPC ............ *C07K 16/40* (2013.01); *A61K 9/0019* (2013.01); *A61K 9/10* (2013.01); *A61K 9/1623* (2013.01); *A61K 9/1694* (2013.01); *A61K 39/39541* (2013.01); *A61K 39/3955* (2013.01); *C07K 16/22* (2013.01); *C07K 16/2887* (2013.01); *C07K 16/32* (2013.01); *C07K 2317/21* (2013.01)

(58) Field of Classification Search
None
See application file for complete search history.

(56) References Cited

U.S. PATENT DOCUMENTS

| | | |
|---|---|---|
| 2,822,316 A | 2/1958 | Hans |
| 3,639,587 A | 2/1972 | Ames |
| 5,747,058 A | 5/1998 | Tipton et al. |
| 6,171,586 B1 | 1/2001 | Lam et al. |
| 6,267,958 B1 | 7/2001 | Andya et al. |
| 6,284,282 B1 | 9/2001 | Maa et al. |
| 6,685,940 B2 | 2/2004 | Andya et al. |
| 6,875,432 B2 | 4/2005 | Liu et al. |
| 7,622,115 B2 | 11/2009 | Fyfe et al. |
| 7,666,413 B2 | 2/2010 | Liu et al. |
| 8,779,094 B2 | 7/2014 | Johnston et al. |
| 2003/0190316 A1 | 10/2003 | Kakuta et al. |
| 2003/0198619 A1 | 10/2003 | Dong et al. |
| 2005/0118163 A1 | 6/2005 | Mizushima et al. |
| 2005/0214278 A1 | 9/2005 | Kakuta et al. |
| 2006/0141040 A1 | 6/2006 | Chen et al. |
| 2008/0071063 A1* | 3/2008 | Allan ..................... A61P 29/00 530/387.1 |
| 2008/0311115 A1 | 12/2008 | Chang |
| 2009/0022727 A1 | 1/2009 | Houston et al. |
| 2009/0074786 A1* | 3/2009 | Dor ...................... A61K 31/436 514/291 |
| 2009/0226530 A1* | 9/2009 | Lassner .................. A61P 25/04 424/490 |
| 2009/0291076 A1 | 11/2009 | Morichika et al. |
| 2010/0285011 A1 | 11/2010 | Morichika et al. |
| 2011/0044977 A1 | 2/2011 | Adler et al. |

(Continued)

FOREIGN PATENT DOCUMENTS

| | | |
|---|---|---|
| DE | 2949849 A1 | 6/1981 |
| EP | 1977763 A1 | 10/2008 |

(Continued)

OTHER PUBLICATIONS

Akers, M.J. et al. (1987). "Formulation Design and Development of Parenteral Suspensions" J Parent Sci & Techn 41(3):88-96.
Alford, J.R. et al. (2008). "High Concentration Formulations of Recombinant Human Interleukin-1 Receptor Antagonist: II. Aggregation Kinetics," J Pharm Sci. 97(8):3005-3021.
Bio Industry. (2010). The Practical Application of Research and Development in the Pharmaceutical Industry Using Human Biomaterials in Japan, 22(7):18-23, (Translation of the Table of Contents and the Abstract).
Communication of a Notice of Opposition from European Patent Office, dated Feb. 8, 2019, for European Application No. 13724493.5, filed on Nov. 26, 2014, Opponent Bayer AG, Proprietor Genentech, Inc., 15 pages.

(Continued)

*Primary Examiner* — Phuong Huynh
(74) *Attorney, Agent, or Firm* — MORRISON & FOERSTER LLP

(57) ABSTRACT

The present application discloses high-concentration monoclonal antibody formulations suitable for subcutaneous administration, e.g. via a pre-filled syringe. In particular, it discloses a formulation comprising a spray dried monoclonal antibody at a concentration of about 200 mg/mL or more suspended in a non-aqueous suspension vehicle where the viscosity of the suspension vehicle is less than about 20 centipoise. Also disclosed are: a subcutaneous administration device with the formulation therein, a method of making the formulation, a method of making an article of manufacture comprising the suspension formulation, use of the formulation in the preparation of a medicament, and a method of treating a patient with the formulation.

20 Claims, 10 Drawing Sheets

Specification includes a Sequence Listing.

(56) References Cited

U.S. PATENT DOCUMENTS

| | | | |
|---|---|---|---|
| 2011/0076273 A1 | 3/2011 | Adler et al. | |
| 2011/0223208 A1* | 9/2011 | Hill | A61K 47/44 424/141.1 |
| 2013/0309226 A1 | 11/2013 | Armstrong et al. | |
| 2020/0087415 A1 | 3/2020 | Armstrong et al. | |

FOREIGN PATENT DOCUMENTS

| | | | |
|---|---|---|---|
| GB | 1225979 A | 3/1971 | |
| JP | 2006503545 A | 2/2006 | |
| JP | 2007501270 A | 1/2007 | |
| JP | 2007537283 A | 12/2007 | |
| JP | 2009521482 A | 6/2009 | |
| JP | 2010530852 A | 9/2010 | |
| JP | 2012509337 A | 4/2012 | |
| JP | 2013522216 A | 6/2013 | |
| KR | 1020050044365 A | 5/2005 | |
| KR | 1020080098504 A | 11/2008 | |
| KR | 1020110103961 A | 9/2011 | |
| WO | 199704801 A1 | 2/1997 | |
| WO | WO-9704801 A1 * | 2/1997 | A61K 39/39591 |
| WO | 200115734 A2 | 3/2001 | |
| WO | 2003039485 A2 | 5/2003 | |
| WO | 2003068934 A2 | 8/2003 | |
| WO | 2004105798 A1 | 12/2004 | |
| WO | 2005112893 A1 | 12/2005 | |
| WO | 2006017852 A2 | 2/2006 | |
| WO | 2006044908 A2 | 4/2006 | |
| WO | 2006083799 A2 | 8/2006 | |
| WO | 2006119968 A2 | 11/2006 | |
| WO | 2007092772 A2 | 8/2007 | |
| WO | 2008092084 A2 | 7/2008 | |
| WO | 2008157161 A1 | 12/2008 | |
| WO | 2010056657 A2 | 5/2010 | |
| WO | 2010059717 A2 | 5/2010 | |
| WO | WO-2010056657 A2 * | 5/2010 | A61K 38/385 |
| WO | 2011012637 A2 | 2/2011 | |

OTHER PUBLICATIONS

Dani, B. et al. (2007). "Pharmaceutics, Preformulation and Drug Delivery. High Concentration Formulation Feasibility of Human Immunoglobulin G for Subcutaneous Administration," J. Pharm. Sci. 96(6):1504-1517.

Dueva-Koganov O.V. et al. (2010). "In Vitro/In Vivo and Analytical Evaluation of Sunless Tanning Formulations Containing Different Rheology Modifiers," J. Cosmet. Sci. 61(2):73-83.

European Patent Office, Summons to Attend Oral Proceedings Pursuant to Rule 115(1) EPC, dated Oct. 23, 2019, filed on Nov. 26, 2014, 21 pages.

Examination Report dated Feb. 26, 2021, for European Patent Application No. 18169218.7, filed on Apr. 25, 2018, 3 pages.

Extended Search Report for European Patent Application No. 18169218.7, dated Oct. 5, 2018, filed on Apr. 25, 2018, 8 pages.

Floyd, A.G. et al. (1996). "Injectable Emulsions and Suspensions" Chapter 7 in Pharmaceutical Dosage Forms: Disperse Systems, Lieberman HA, Rieger MM, Banker GS, Dekker, NY, NY: vol. 2:261-318.

He, F. et al. (2011). "Screening of Monoclonal Antibody Formulations Based on High-Throughput Thermostability and Viscosity Measurements: Design of Experiment and Statistical Analysis," J Pharm Sci. 100(4):1330-1340.

Heintz, A.M. et al. "Engineered Drug Delivery—Enabling Bolus Injections of High Viscosity MAb Formulations (Battelle The Business of Innovation)" Slides pp. 1-18.

Hirano, K. et al. (1982). "Studies on the Absorption of Practically Water-Insoluble Drugs Following Injection V: Subcutaneous Absorption in Rats From Solutions in Water Immiscible Oils," J. Pharm. Sci. 71(5):495-500.

International Search Report dated Jul. 12, 2013, for PCT Application No. PCT/US2013/041532, pp. 1-5.

Kanai, S. et al. (2008). "Reversible Self-Association of a Concentrated Monoclonal Antibody Solution Mediated by Fab-Fab Interaction That Impacts Solution Viscosity," J. Pharm. Sci. 97(10):4219-4227.

Karasulu, H.Y. et al. (2007). "Controlled Release of Methotrexate From W/O Microemulsion and its in Vitro Antitumor Activity," Drug Deliv. 14(4):225-233.

Kunitz, M. (1926). "An Empirical Formula For The Relation Between Viscosity Of Solution And Volume Of Solute," J. Gen. Physiol. 9(6):715-725.

Larsen, S.W. et al. (2006). "In Vitro Assessment of Drug Release Rates From Oil Depot Formulations Intended for Intra-Articular Administration," Eur. J. Pharm. Sci. 29(5):348-354.

Lee, G. (2002). "Rational Protein Formulation: Theory and Practice Spray Drying of Proteins," Carpenter J. et al., Plenum Press Edition, Pharmaceutical Biotechnology Series, pp. 135-158.

Maa, Y-F. et al. (1997). "The Effect of Operating and Formulation Variables on the Morphology of Spray-Dried Protein Particles" Pharm. Dev. Technol. 2(3):213-223.

Maa, Y-F. et al. (1998). "Spray-Drying of Air-Liquid Interface Sensitive Recombinant Human Growth Hormone," J. Pharm. Sci. 87(2):152-159.

Maa, Y.F. et al. (1998). "Spray-Drying Performance of a Bench-Top Spray Dryer for Protein Aerosol Powder Preparation" Biotechnol. Bioeng. 60(3):301-309.

Mahjour, M. et al. (1999). "Effects of Propylene Glycol Diesters of Caprylic and Capric Acids (Miglyol® 840) and Ethanol Binary Systems on in Vitro Skin Permeation of Drugs," Intl. J. Pharm. 95:161-169.

Maury, M. et al. (2005). "Effects of Process Variables on the Powder Yield of Spray-Dried Trehalose on a Laboratory Spray-Dryer," Eur. J. Pharm. Biopharm. 59(3):565-573.

Miller, M. et al. (2010). "Low Viscosity Highly Concentrated Injectable Nonaqueous Suspensions of Lysozyme Microparticles" Langmuir 26(2):1067-1074.

Mottu, F. et al. (2000). "Organic Solvents for Pharmaceutical Parenterals and Embolic Liquids: A Review of Toxicity Data," PDA J. Pharm. Sci. Technol. 54(6):456-469.

Overcashier, D.E. et al. (2006). "Technical Considerations in the Development of Pre-filled Syringes for Protein Products," Am. Pharm. Rev. 9(7):77-83.

Pena, L.E. et al. (1995). "Rheological Characterization of rbSt Oil Suspensions," Intl. J. Pharm. 113:89-96.

Salinas, B.A. et al. (2010). "Understanding and Modulating Opalescence and Viscosity in a Monoclonal Antibody Formulation," J. Pharm. Sci. 99(1):82-93.

Salmeron, M.D. et al. (1997). "Encapsulation Study of 6-Methylprednisolone in Lipid Microspheres," Drug Dev. Ind. Pharm. 23:131-136.

Santucci, E. et al. (1996). "Gellan for the Formulation of Sustained Delivery Beads," J. Contr. Rel. 42:157-164.

Seniro. (1999). "Final Report on the Safety Assessment of Propylene Glycol (PG) Dicaprylate, PG Dicaprylate/Dicaprate, PG Dicocoate, PG Dipelargonate, PG Isostearate, PG Laurate, PG Myristate, PG Oleate, PG Oleate SE, PG Dioleate, PG Dicaprate, PG Diisostearate, and PG Dilaurat" Intl J Toxicol 18(Supp. 2):35-52.

Shire, S. J. et al. (2004). "Challenges in the Development of High Protein Concentration Formulations," J. Pharm. Sci. 93(6):1390-1402.

Spiegel, A.J. et al. (1963). "Use of Nonaqueous Solvents in Parenteral Products," J. Pharm. Sci. 52:917-927.

Stancovski, I. et al. (1991). "Mechanistic Aspects of the Opposing Effects of Monoclonal Antibodies to the ERBB2 Receptor on Tumor Growth," Proc. Natl. Acad. Sci. USA 88:8691-8695.

Stockwin, L.H. et al. (2003). "Antibodies as Therapeutic Agents: Vive La Renaissance," Expert Opin, Biol. Ther. 3(7):1133-1152.

Sukumar, M. et al., (2004). "Opalescent Appearance of an IgGl Antibody at High Concentrations and its Relationship to Noncovalent Association," Pharm. Res. 21(7): 1087-1093.

Suzuki. (2010). "Difficulties Faced in the Research and Development of Pharmaceutical Products Using Human Organs, Tissue, and Cells in Japan," Bio. Industry 27(2):18-23. (Translation of the Abstract Only).

(56) References Cited

OTHER PUBLICATIONS

Thielmann, F. (2006). "Inverse gas chromatography: Characterization of alumina and related surfaces" in Encyclopedia of Surface and Colloid Science, P. Somasundaran, Boca Raton, FL.:CRC Press, vol. 4:3009-3017.

Thielmann, F. et al. (2007). "Heat of Sorption on Microcrystalline Cellulose by Pulse Inverse Gas Chromatography at Infinite Dilution," Surface Measurement Services Application Note 203 (http://www.thesorptionsolution.com/InformationApplication_Notes JGC.php#Aps), 3 pages.

Trilisky, E. et al. (2011, e-pub. Jun. 8, 2011). "Crystallization and Liquid-Liquid Phase Separation of Monoclonal Antibodies and Fc-Fusion Proteins: Screening Results," AICHE Biotechnol. Prog. 27(4):1054-1067.

Written Opinion dated Jul. 18, 2013, for PCT Application No. PCT/US2013/041532, filed on May 17, 2013, 4 pages.

Yang, M.X. et al. (2003). "Crystalline Monoclonal Antibodies for Subcutaneous Delivery," Proc. Natl. Acad. Sci. USA 100(12):6934-6939.

Yu, L. et al. (2008). "Interaction Between Bevacizumab and Murine VEGF-A: A Reassessment," Investigative Opthalmology & Visual Science 49(2):522-527.

\* cited by examiner

FIG. 8A-1

Rituximab Heavy Chain

```
    +1      FR1                                                           15
    Gln Val Gln Leu Gln Gln Pro Gly Ala Glu Leu Val Lys Pro Gly Ala Ser
             20                  25                  30  31       CDR1  35  36
Val Lys Met Ser Cys Lys Ala Ser Gly Tyr Thr Phe Thr Ser Tyr Asn Met His Trp
             40  FR2                 45                  49  50      52 52A 53  54
Val Lys Gln Thr Pro Gly Arg Gly Leu Glu Trp Ile Gly Ala Ile Tyr Pro Gly Asn
55          CDR2        60                  65  66  FR3         70
Gly Asp Thr Ser Tyr Asn Gln Lys Phe Lys Gly Lys Ala Thr Leu Thr Ala Asp Lys
    75                  80              82 82A 82B 82C 83      85
Ser Ser Thr Ala Tyr Met Gln Leu Ser Ser Leu Thr Ser Glu Asp Ser Ala Val
    90      94 95 CDR3                100 100A 100B 100C 100D 101 102 103
Tyr Tyr Cys Ala Arg Ser Thr Tyr Tyr Gly Gly Asp Trp Tyr Phe Asn Val Trp Gly
105 FR4         110              113 114                        120
Ala Gly Thr Thr Val Thr Val Ser Ala Ala Ser Thr Lys Gly Pro Ser Val Phe Pro
130 133         Human Gamma 1 Constant      140
Leu Ala Pro Ser Ser Lys Ser Thr Ser Gly Gly Thr Ala Ala Leu Gly Cys Leu Val
                            150             154 156 157 162
Lys Asp Tyr Phe Pro Glu Pro Val Thr Val Ser Trp Asn Ser Gly Ala Leu Thr Ser
169 171                                     180 182
Gly Val His Thr Phe Pro Ala Val Leu Gln Ser Ser Gly Leu Tyr Ser Leu Ser Ser
190                                         200 203 205         210
Val Val Thr Val Pro Ser Ser Ser Leu Gly Thr Gln Thr Tyr Ile Cys Asn Val Asn
```

FIG. 8A
- FIG. 8A-1
- FIG. 8A-2

His Lys Pro Ser Asn Thr Lys Val Asp Lys Lys Ala Glu Pro Lys Ser Cys Asp Lys
                240                220  222/225         250          230 232 235
                                       243 244

Thr His Thr Cys Pro Pro Cys Pro Ala Pro Glu Leu Leu Gly Gly Pro Ser Val Phe
260                             270

Leu Phe Pro Pro Lys Pro Lys Asp Thr Leu Met Ile Ser Arg Thr Pro Glu Val Thr
280                             290      292

Cys Val Val Val Asp Val Ser His Glu Asp Pro Glu Val Lys Phe Asn Trp Tyr Val
295 296 299 300                         310                      314 317

Asp Gly Val Glu Val His Asn Ala Lys Thr Lys Pro Arg Glu Glu Gln Tyr Asn Ser
320                             330

Thr Tyr Arg Val Val Ser Val Leu Thr Val Leu His Gln Asp Trp Leu Asn Gly Lys
340                             350                                      355

Glu Tyr Lys Cys Lys Val Ser Asn Lys Ala Leu Pro Ala Pro Ile Glu Lys Thr Ile
357 360 361 363                         370

Ser Lys Ala Lys Gly Gln Pro Arg Glu Pro Gln Val Tyr Thr Leu Pro Pro Ser Arg
378 381                                 390

Asp Glu Leu Thr Lys Asn Gln Val Ser Leu Thr Cys Leu Val Lys Gly Phe Tyr Pro
    400         402 405         408 410 413                          420

Ser Asp Ile Ala Val Glu Trp Glu Ser Asn Gly Gln Pro Glu Asn Asn Tyr Lys Thr
            428 430 433                             440

Thr Pro Pro Val Leu Asp Ser Asp Gly Ser Phe Phe Leu Tyr Ser Lys Leu Thr Val
                450                                 460

Asp Lys Ser Arg Trp Gln Gln Gly Asn Val Phe Ser Cys Ser Val Met His Glu Ala
                470                                 478

Leu His Asn His Tyr Thr Gln Lys Ser Leu Ser Leu Ser Pro Gly Lys TER

Amino Acid # (Kabat)

FIG. 8A-2

Rituximab Light Chain

```
     +1    FR1                                              10
     Gln Ile Val Leu Ser Gln Ser Pro Ala Ile Leu Ser Ala Ser
            20            23|24 CDR1  27|                   34
     Pro Gly Glu Lys Val Thr Met Thr Cys|Arg Ala Ser Ser Ser Val Ser Tyr Ile His|
     35              FR2                  45                       49|50    CDR2
     Trp Phe Gln Gln Lys Pro Gly Ser Ser Pro Lys Pro Trp Ile Tyr|Ala Thr Ser Asn
     55      56|57                    FR3 65                                70
     Leu Ala Ser|Gly Val Pro Val Arg Phe Ser Gly Ser Gly Ser Gly Thr Ser Tyr Ser
             75                       80                   85            88|89  90
     Leu Thr Ile Ser Arg Val Glu Ala Ala Asp Ala Ala Thr Tyr Tyr Cys|Gln Gln Trp
                 95   97|98      100 FR4                     105     107|108   110
     Thr Ser Asn Pro Pro Thr|Phe Gly Gly Gly Thr Lys Leu Glu Ile Lys|Arg Thr Val
                                              120
     Ala Ala Pro Ser Val Phe Ile Phe Pro Pro Ser Asp Glu Gln Leu Lys Ser Gly Thr
     130                              Human Kappa Constant
                                              140
     Ala Ser Val Val Cys Leu Leu Asn Asn Phe Tyr Pro Arg Glu Ala Lys Val Gln Trp
     150                                      160
     Lys Val Asp Asn Ala Leu Gln Ser Gly Asn Ser Gln Glu Ser Val Thr Glu Gln Asp
             170                              180
     Ser Lys Asp Ser Thr Tyr Ser Leu Ser Ser Thr Leu Thr Leu Ser Lys Ala Asp Tyr
                     190                              200
     Glu Lys His Lys Val Tyr Ala Cys Glu Val Thr His Gln Gly Leu Ser Ser Pro Val
                             210                  214
     Thr Lys Ser Phe Asn Arg Gly Glu Cys TER                      Amino Acid # (kabat)
```

FIG. 8B

Bevacizumab Heavy Chain

EVQLVESGGGLVQPGGSLRLSCAAS<u>GYTFTNYGMN</u>WVRQAPGKGLEWVG<u>WINTYTGE
PTYAADFKRR</u>FTFSLDTSKSTAYLQMNSLRAEDTAVYYCAKY<u>PHYYGSSHWYFDV</u>WG
QGTLVTVSS‖ASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCD
KTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLSLSPGK

*FIG. 9A*

Bevacizumab Light Chain

DIQMTQSPSSLSASVGDRVTITC<u>SASQDISNYLN</u>WYQQKPGKAPKVLIY<u>FTSSLHS</u>G
VPSRFSGSGSGTDFTLTISSLQPEDFATYYC<u>QQYSTVPWT</u>FGQGTKVEIKR‖TVAAP
SVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

*FIG. 9B*

TRASTUZUMAB Heavy Chain

```
  1                            15                             30                            45
  E V Q L V E S G G G L V Q P G G S L R L S C A A S G F N I K D T Y I H W V R Q A P G K G L
                                                             CDR H1
 46                            60                             75                            90
  E W V A R I Y P T N G Y T R Y A D S V K G R F T I S A D T S K N T A Y L Q M N S L R A E D
              CDR H2
 91                           105                            120                           135
  T A V Y Y C S R W G G D G F Y A M D Y W G Q G T L V T V S S A S T K G P S V F P L A P S S
                   CDR H3
136                           150                            165                           180
  K S T S G G T A A L G C L V K D Y F P E P V T V S W N S G A L T S G V H T F P A V L Q S S
181                           195                            210                           225
  G L Y S L S S V V T V P S S S L G T Q T Y I C N V N H K P S N T K V D K K V E P K S C D K
226                           240                            255                           270
  T H T C P P C P A P E L L G G P S V F L F P P K P K D T L M I S R T P E V T C V V V D V S
271                           285                            300                           315
  H E D P E V K F N W Y V D G V E V H N A K T K P R E E Q Y N S T Y R V V S V L T V L H Q D
316                           330                            345                           360
  W L N G K E Y K C K V S N K A L P A P I E K T I S K A K G Q P R E P Q V Y T L P P S R E E
361                           375                            390                           405
  M T K N Q V S L T C L V K G F Y P S D I A V E W E S N G Q P E N N Y K T T P P V L D S D G
406                           420                            435             449
  S F F L Y S K L T V D K S R W Q Q G N V F S C S V M H E A L H N H Y T Q K S L S L S P G
```

FIG. 10A

TRASTUZUMAB Light Chain

```
1                        15                        30                        45
DIQMTQSPSSLSASVGDRVTITC RASQDVNTAVA WYQQKPGKAPK
                                       CDRL1
46                       60                        75                        90
LLIY SASFLYS GVPSRFSGSRSGTDFTLTISSLQPEDFATYYC QQ
     CDRL2
91                       105                       120                       135
HYTTPPT FGQGTKVEIKRT VAAPSVFIFPPSDEQLKSGTASVVCL
CDRL3
136                      150                       165                       180
LNNFYPREAKVQWKVDNALQSGNSQESVTEQDSKDSTYSLSSTLT
181                      195                       210  214
LSKADYEKHKVYACEVTHQGLSSPVTKSFNRGEC
```

FIG. 10B

HIGH-CONCENTRATION MONOCLONAL ANTIBODY FORMULATIONS

This non-provisional application is a continuation application of U.S. patent application Ser. No. 16/383,270, filed on Apr. 12, 2019, now abandoned, which is a continuation application of U.S. patent application Ser. No. 14/752,670, filed on Jun. 26, 2015, now abandoned, which is a continuation application of U.S. patent application Ser. No. 13/896,622, filed on May 17, 2013, now abandoned, which claims the benefit under 35 USC § 119(e) of U.S. Provisional Application Ser. No. 61/649,146, filed on May 18, 2012, the contents of each of which are incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392026703SEQLIST.TXT, date recorded: Oct. 28, 2020, size: 27 KB).

FIELD OF THE INVENTION

The present invention concerns high-concentration monoclonal antibody formulations suitable for subcutaneous administration, e.g. via a pre-filled syringe. In particular, the invention concerns a formulation comprising a spray dried monoclonal antibody at a concentration of about 200 mg/mL or more suspended in a non-aqueous suspension vehicle, wherein the viscosity of the suspension vehicle is less than about 20 centipoise. The invention also concerns a subcutaneous administration device with the formulation therein, a method of making the suspension formulation, a method of making an article of manufacture comprising the suspension formulation, use of the suspension formulation in the preparation of a medicament, and a method of treating a patient with the suspension formulation.

BACKGROUND OF THE INVENTION

Outpatient administration of high-dose monoclonal antibodies (several mg per kg) via subcutaneous (SC) injection is a preferred form of delivery for treating chronic conditions (Stockwin and Holmes, *Expert Opin Biol Ther* 3:1133-1152 (2003); Shire et al., *J Pharm Sci* 93:1390-1402 (2004)). The subcutaneous route of administration that requires injections using syringes, auto-injectors, or other devices generally restricts product formulation with regards to injection volume and solution viscosity, and device functionalities in terms of injection force and time. To deliver high-dose of monoclonal antibody with limitations of injection time, volume, and force, a high-concentration monoclonal antibody formulation (100 mg/mL or greater) is required for subcutaneous administration (Stockwin and Holmes, *Expert Opin Biol Ther* 3:1133-1152 (2003); Shire et al., *J Pharm Sci* 93:1390-1402 (2004)). A potential challenge in the development of high protein concentration formulations is concentration-dependent solution viscosity. Injection force (or glide force) is a complex factor influenced by solution viscosity, the size of the needle (i.e., needle gauge), and surface tension of container/closure. Smaller needles, e.g., ≥26 gauge, will pose less pain sensation to the patients. Overcashier and co-workers established a viscosity-glide force relationship as a function of needle gauge based on Hagen-Poiseuille Equation (Overcashier et al., *Am. Pharm Rev.* 9(6):77-83 (2006)). With a 27-gauge thin walled (TW) needle (ID, min.: 0.241 mm), the liquid viscosity should be maintained below 20 centipoise in order not to exceed the glide force of 20 newton. Unfortunately, formulation scientists are constantly challenged against a conflicting reality with high monoclonal antibody concentration and high solution viscosity (Shire et al., *J Pharm Sci* 93:1390-1402 (2004); Kanai et al., *J Pharm Sci* 97:4219-4227 (2005)). Another challenge with liquid formulations at high monoclonal antibody concentration is protein physical stability. Greater aggregation rates and undesirable opalescence are generally observed in high monoclonal antibody concentration liquid solutions (Alford et al., *J Pharm Sci* 97:3005-3021 (2008); Salinas et al., *J Pharm Sci* 99:82-93 (2010); Sukumar et al., *Pharm Res* 21:1087-1093 (2004)).

Different formulation strategies have been attempted to reduce the viscosity of high-concentration monoclonal antibody liquid solution by formulating with salt, amino acid, or sugar to balance repulsive and attractive forces through intermediate ionic strengths (Sukumar et al., *Pharm Res* 21:1087-1093 (2004); He et al., *J Pharm Sci* 100:1330-1340 (2011)). However, the effectiveness of these approaches may be limited at monoclonal antibody concentration beyond 100 mg/mL or due to specific characteristics of certain monoclonal antibodies. Dani and co-workers applied the approach of reconstituting spray-dried monoclonal antibody powder to prepare high monoclonal antibody concentration liquid solution prior to subcutaneous injection (Dani et al., *J Pharm Sci* 96:1504-1517 (2007)). This approach can certainly improve the protein stability in the solid state during the entire shelf life, however the high viscosity issue still remains because the spray dried monoclonal antibody powder needs to be reconstituted at high monoclonal antibody concentration prior to injection. A powder-based approach emerged recently using monoclonal antibody crystalline particle suspensions (Yang et al., *Proc Natl Acad Sci* 100: 6934-6939 (2003); Trilisky et al., "Crystallization and liquid-liquid phase separation of monoclonal antibodies and Fc-fusion proteins: Screening results," AICHE online publication DOI 10, 1002/btrp.621 (published by Wiley Online Library) (2011)). It is based on the perception that viscosity of a crystal monoclonal antibody suspension may be lower than a liquid formulation at the same monoclonal antibody concentration. However, no viscosity or injection force data were presented in these references and this concept remained speculative. Furthermore, monoclonal antibody crystallization is not yet a mature process platform applicable to a wide range of monoclonal antibodies although some successful examples have been presented (Trilisky et al., "Crystallization and liquid-liquid phase separation of monoclonal antibodies and Fc-fusion proteins: Screening results," AICHE online publication DOI 10, 1002/btrp.621 (published by Wiley Online Library) (2011)).

The present invention represents a different powder-based concept employing a high-concentration monoclonal antibody powder suspension in a non-aqueous suspension vehicle. The suspension approach has been comprehensively reviewed (Floyd and Jain, "Injectable emulsions and suspensions," In: *Pharmaceutical Dosage Forms: Disperse Systems* Volume 2 (eds. Lieberman H A, Rieger M M, Banker G S). Dekker. NY, NY, p 261-318 (1996); Akers et al., *J Parent Sci & Techn* 41:88-96 (1987)) and has been reported for microsphere/emulsion suspensions in vegetable oils, such as sesame oil (Larsen et al., *Eur J Pharm Sci* 29:348-354 (2006); Hirano et al., *J Pharm Sci* 71:495-500 (1982)), soybean oil (Salmerón et al., *Drug Dev Ind Pharm*

23:133-136 (1997); Karasulu et al., *Drug Dev* 14:225-233 (2007)), and peanut oil (Santucci et al., *J Contr Rel* 42:157-164 (1996)) as parenteral injectables. The physical and chemical forces influencing the properties of non-aqueous suspensions can be quite different from those of aqueous suspension due to the absence of electrical effects associated with the DLVO theory (van der Waals attraction and electrostatic repulsion as the result of double layer of counterions).

Pena and co-workers (Pena et al., *Intl J Pharm* 113:89-96 (1995)) reported rheological characterization of excipient-free bovine somatotropin (rbSt) powder (lyophilized or spray-dried) suspension in caprylic/capric triglyceride (MIGLYOL 812®) oil with or without polysorbate 80. RbSt is a 191-amino acid peptide with a molecular weight of 22,000 daltons. Pena et al. determined that a network formed among drug particle, polysorbate 80, and MIGLYOL 812®, and a higher viscosity was observed with increasing polysorbate 80 and powder concentrations. These studies also found that particle shape/morphology played an important role in suspension viscosity. The smaller spherical (more densely packed) spray-dried particles resulted in more viscous suspensions than the lyophilized counterpart which displayed larger irregular shaped flakes.

The non-aqueous powder-based approach for high concentration monoclonal antibody concentration suspensions remains unexplored. Studies with the small rbSt peptide in Pena et al. would not predict the ability to effectively formulate a large tetrameric monoclonal antibody (about 150,000 daltons). In addition, the oil vehicles used by Pena et al. were too viscous to be considered for use in pre-filled syringe administration. The viscosity of MIGLYOL 812®, sesame oil, soybean oil, peanut oil are ~30 centipoise (cP) at 25° C., 43 cP at 25° C., 50 cP at 25° C. and 35 cP at 37° C., respectively. In addition, Pena et al. determined the suspension performance of spray dried powder was inferior to lyophilized counterpart.

Publications describing monoclonal antibody formulations include: U.S. Pat. No. 6,284,282 (Maa et al.); U.S. Pat. Nos. 6,267,958 and 6,685,940 (Andya et al.); U.S. Pat. No. 6,171,586 (Lam et al.); U.S. Pat. Nos. 6,875,432 and 7,666,413 (Liu et al.); WO2006/044908 (Andya et al.); US-2011-0076273-A1 (Adler et al.); US 2011/0044977 and WO 2011/012637 (Adler et al.); US 2009/0226530A 1 (Lassner et al.); US-A 2003/0190316 (Kakuta et al.); US-A 2005/0214278 and US-A 2005/0118163 (Mizushima et al.); US-A 2009/0291076 (Morichika et al.); and US-A 2010/0285011 (Imaeda et al.)

SUMMARY OF THE INVENTION

The objectives of the present study were to: (1) identify process parameters that dictate suspension performance; (2) assess the feasibility of establishing monoclonal antibody powder suspensions (i.e. ≥250 mg monoclonal antibody/mL) with acceptable injectability (i.e. injection force ≤20 N through 27-gauge thin-walled (TW) needle) and physical suspension stability; and/or (3) understand the mechanism of suspension performance. To prepare monoclonal antibody powders, spray drying was used. Spray drying is a mature, scalable, and efficient manufacturing process. The short-term effect of spray drying on monoclonal antibody was studied at accelerated temperature. An important criterion for suspension vehicle selection was that the viscosity of the suspension vehicle be below 10 centipoise (cP). The three model suspension vehicles, propylene glycol dicaprylate/dicaprate, benzyl benzoate, and ethyl lactate, tested in this study have low viscosity and met this requirement.

Inverse gas chromatography (IGC) has been used for surface energy analysis (SEA) (Newell et al., *Pharm Res* 18:662-666 (2001); Grimsey et al., *J Pharm Sci* 91:571-583 (2002); Newell and Buckton, *Pharm Res* 21:1440-1444 (2004); Saleem and Smyth, *Drug Devel & Ind Pharm* 34:1002-1010 (2008); Panzer and Schreiber, *Macromolecules* 25:3633-3637 (1992)). In IGC, a probe is injected into a column packed with the powder of interest (stationary phase) and the time required for the probe to pass through the column ($t_r$) is a measure of the magnitude of the interaction between the probe and the stationary phase. Surface energy can normally be divided into polar and dispersive (non-polar) components. Thus, the use of non-polar (alkanes) and polar (electron acceptor-donor or acid-base solvents) probes allowed these two surface energy components to be quantified. Surface energies of the spray-dried particles may serve as a more direct and relevant indicator to suspension performance than other particle characteristics. Another parameter is heat of sorption which is a direct measure of the strength of the interactions between a solid and gas molecules adsorbed on the surface (Thielmann F., "Inverse gas chromatography: Characterization of alumina and related surfaces," In "*Encyclopedia of Surface and Colloid Science* Volume 4 (edit by P. Somasundaran). CRC Press, Boca Raton, FL., p 3009-3031 (2006); Thielmann and Butler, "Heat of sorption on microcrystalline cellulose by pulse inverse gas chromatography at infinite dilution," Surface Measurement Services Application Note 203 (http://www.thesorptionsolution.com/lnformation_Application_Notes_IGC.php #Aps) (2007)). The IGC method was employed to measure the heat of sorption between spray dried particles and the suspension vehicle in this study.

The experimental data herein demonstrate that the objectives were achieved, and high-concentration monoclonal antibody suspension formulations suitable for subcutaneous administration were developed.

Thus, in a first aspect, the invention concerns a suspension formulation comprising a spray dried monoclonal antibody at a concentration of about 200 mg/mL or more suspended in a non-aqueous suspension vehicle, wherein the viscosity of the suspension vehicle is less than about 20 centipoise.

In another aspect, the invention concerns a suspension formulation comprising a spray dried full length human IgG1 monoclonal antibody at a concentration from about 200 mg/mL to about 400 mg/mL suspended in a non-aqueous suspension vehicle with a viscosity less than about 20 centipoise, wherein the formulation has an average particle size from about 2 microns to about 10 microns, and injection glide force less than about 15 newton.

The invention further concerns a subcutaneous administration device (e.g. a pre-filled syringe) with the formulation therein.

In another aspect, the invention concerns a method of making a suspension formulation comprising suspending a spray dried monoclonal antibody in a non-aqueous suspension vehicle with a viscosity less than about 20 centipoise, wherein the antibody concentration in the suspension formulation is about 200 mg/mL or more.

Additionally, the invention provides a method of making an article of manufacture comprising filling a subcutaneous administration device with the formulation herein.

In related aspects, the invention concerns use of the formulation in the preparation of a medicament for treating a patient in need of treatment with the monoclonal antibody in the formulation, as well as a method of treating a patient comprising administering the formulation to a patient in need of treatment with the monoclonal antibody in the formulation.

Figure 1:
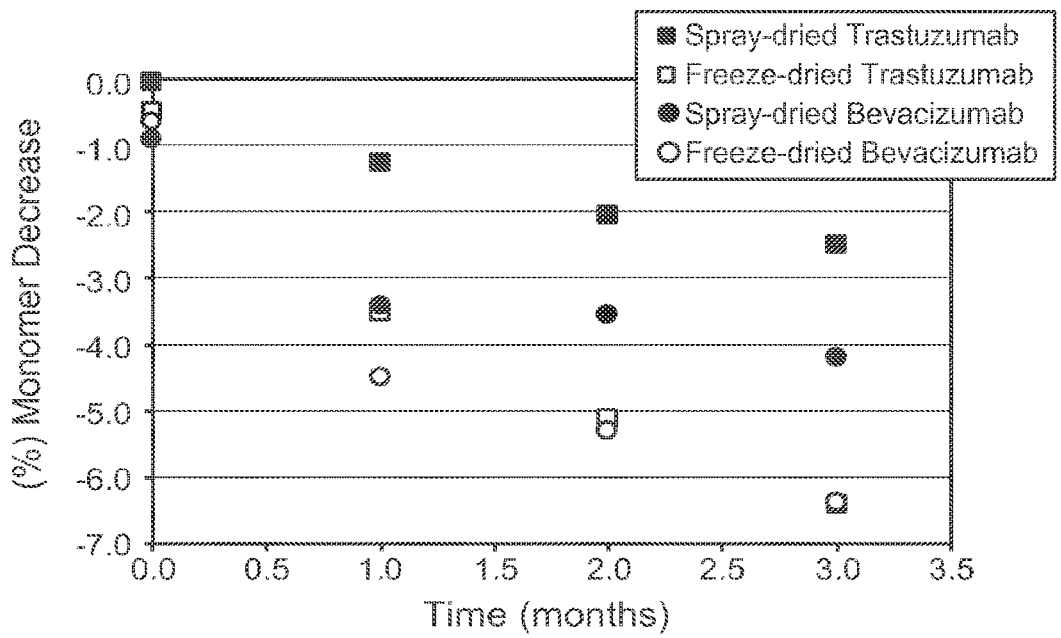
FIG. 1: Antibody stability (as size exclusion chromatography (SEC) % monomer change from right after spry drying) as a function of storage time at 40° C. for bevacizumab/trehalose formulation spray-dried (●) and freeze dried (○) as well as for trastuzumab/trehalose formulation spray dried (■) and freeze dried (□).

FIGS. 6A-C: Photographs of rituximab suspension at 150 mg/mL in ethyl lactate after 2-week storage (6A), in ethyl lactate vortexed after 1-day storage (6B), and in propylene glycol dicaprylate/dicaprate after 2 weeks storage (6C). (Note: the tape is not part of the suspension but used for optical focusing during photo taking.)

FIGS. 7A and 7B: Rituximab suspensions. FIG. 7A: Particle size distribution of rituximab suspensions in mixtures of propylene glycol dicaprylate/dicaprate and ethyl lactate at 100/0 (◇), 75/25 (■), 50/50 (□), 25175 (♦), and 0/100 (Δ). FIG. 7B: Photograph of rituximab suspension in 75/25 propylene glycol dicaprylate/dicaprate/ethyl lactate mixture after 2-week storage. (Note: the tape is not part of the suspension but used for optical focusing during photo taking.)

FIGS. 8A-1, 8A-2 and 8B provide the amino acid sequences of the heavy chain (SEQ ID No. 1) and light chain (SEQ ID No. 2) of rituximab antibody. Each of the framework regions (FR) and each of the complementarity determining region (CDR) regions in each variable region are identified, as are the human gamma 1 heavy chain constant sequence and human kappa light chain constant sequence. The variable heavy (VH) region is in SEQ ID No. 3. The variable light (VL) region is in SEQ ID No. 4. The sequence identifiers for the CDRs are: CDR H1 (SEQ ID No. 5), CDR H2 (SEQ ID No. 6), CDR H3 (SEQ ID No. 7), CDR Lt (SEQ ID No. 8), CDR L2 (SEQ ID No. 9), and CDR L3 (SEQ ID No. 10).

FIGS. 9A and 9B provide the amino acid sequences of the heavy chain (SEQ ID No. 11) and light chain (SEQ ID No. 12) of bevacizumab antibody. The end of each variable region is indicated with ||. The variable heavy (VH) region is in SEQ ID No. 13. The variable light (VL) region is in SEQ ID No. 14. Each of the three CDRs in each variable region is underlined. The sequence identifiers for the CDRs are: CDR H1 (SEQ ID No. 15), CDR H2 (SEQ ID No. 16), CDR H3 (SEQ ID No. 17), CDR L1 (SEQ ID No. 18), CDR L2 (SEQ ID No. 19), and CDR L3 (SEQ ID No. 20).

FIGS. 10A and 10B provide the amino acid sequences of the heavy chain (SEQ ID No. 21) and light chain (SEQ ID No. 22) of trastuzumab antibody. The end of each variable region is indicated with ||. The variable heavy (VH) region is in SEQ ID No. 23. The variable light (VL) region is in SEQ ID No. 24. Each of the three CDRs in each variable region is boxed. The sequence identifiers for the CDRs are: CDR H1 (SEQ ID No. 25), CDR H2 (SEQ ID No. 26). CDR H3 (SEQ ID No. 27), CDR L1 (SEQ ID No. 28). CDR L2 (SEQ ID No. 29), and CDR L3 (SEQ ID No. 30).

DETAILED DESCRIPTION OF THE PREFERRED EMBODIMENTS

I. Definitions

The term "pharmaceutical formulation" refers to a preparation which is in such form as to permit the biological activity of the active agent (e.g. monoclonal antibody) to be effective, and which contains no additional components which are unacceptably toxic to a subject to which the formulation would be administered. Such formulations are sterile. In one embodiment, the pharmaceutical formulation is suitable for subcutaneous administration.

"Pharmaceutically acceptable" with respect to an excipient in a pharmaceutical formulation means that the excipient is suitable for administration to a human patient.

A "sterile" formulation is asceptic or free from all living microorganisms and their spores.

"Subcutaneous administration" refers to administration (of a formulation) under the skin of a subject or patient.

A "stable" formulation is one in which the active agent (e.g. monoclonal antibody) therein essentially retains its physical stability and/or chemical stability and/or biological activity upon suspension and/or storage. Preferably, the formulation essentially retains its physical and chemical stability, as well as its biological activity upon suspension and storage. The storage period is generally selected based on the intended shelf-life of the formulation. Various analytical techniques for measuring protein stability are available in the art and are reviewed in *Peptide and Protein Drug Delivery,* 247-301, Vincent Lee Ed., Marcel Dekker, Inc., New York, New York, Pubs. (1991); and Jones, A. *Adv. Drug Delivery Rev.* 10: 29-90 (1993), for example. In one embodiment, stability of the suspension formulation is assessed around the time the spray dried particles are suspended in the vehicle to produce the suspension formulation. In one embodiment, stability can be evaluated when the formulation is held at a selected temperature for a selected time period. In one embodiment, monoclonal antibody stability is assessed by size distribution (percentage monomer, aggregation, and/or fragmentation) before and after spray drying (e.g. before and after spray drying over 3-month storage under the accelerated temperature of 40° C.). In one embodiment, size distribution is assessed using size exclusion chromatography-high performance liquid chromatography (SEC-HPLC). In one embodiment, the percentage monomer loss (as measured by SEC-HPLC) over 3 months is less than about 10%, for example less than 5%, e.g. at accelerated temperature of 40° C. In one embodiment, stability is assessed by evaluating suspension physical stability, e.g. visual inspection of settling and/or particle sedimentation rate.

"Spray drying" refers to the process of atomizing and drying a liquid or slurry comprising a protein or monoclonal antibody using gas (usually air or nitrogen) at a temperature above ambient temperature so as to produce dry powder particles comprising the protein or monoclonal antibody. During the process, liquid evaporates and dry particles form. In one embodiment, the spray drying is performed using a spray dryer, e.g. which has an air inlet temperature from about 100° C. to about 220° C. and an air outlet temperature from about 50° C. to about 100° C. Particles can be separated from the gas by various methods such as cyclone, high pressure gas, electrostatic charge, etc. This definition of spray drying herein expressly excludes freeze drying or crystallizing the monoclonal antibody.

A "dry" particle, protein, or monoclonal antibody herein has been subjected to a drying process such that its water content has been significantly reduced. In one embodiment, the particle, protein, or monoclonal antibody has a water content of less than about 10%, for example less than about 5%, e.g., where water content is measured by a chemical titration method (e.g. Karl Fischer method) or a weight-loss method (high-temperature heating).

For the purposes herein, a "pre-spray dried preparation" refers to a preparation of the monoclonal antibody (usually a recombinantly produced monoclonal antibody which has been subjected to one or more purification steps) and one or more excipients, such as stabilizers (e.g. saccharides, surfactants, and/or amino acids) and, optionally, a buffer. In one embodiment the preparation is in liquid form. In one embodiment the preparation is frozen.

A "suspension formulation" is a liquid formulation comprising solid particles (e.g. spray dried monoclonal antibody particles) dispersed throughout a liquid phase in which they are not soluble. In one embodiment, the solid particles in the suspension formulation have an average particle diameter from about 2 to about 30 microns, e.g. from about 5 to about 10 microns (e.g. as analyzed by laser diffraction). Optionally, the solid particles in the suspension formulation have a peak (highest percentage) particle size of less than about 30 micron, and optionally less than about 10 microns (e.g. as analyzed by laser diffraction). The suspension formulation may be prepared by combining spray dried monoclonal antibody particles with a non-aqueous suspension vehicle. In one embodiment, the suspension formulation is adapted for, or suitable for, subcutaneous administration to a subject or patient.

As used herein "non-aqueous suspension vehicle" refers to a pharmaceutically acceptable liquid which is not water-based and in which spray dried monoclonal antibody particles can be suspended in order to generate a suspension formulation. In one embodiment, the vehicle comprises a liquid lipid or fatty acid ester or alcohol (e.g. propylene glycol dicaprylate/dicaprate), or other organic compound such benzyl benzoate or ethyl lactate. The vehicle herein includes mixtures of two or more liquids, such as a mixture of propylene glycol dicaprylate/dicaprate and ethyl lactate. Preferably, the non-aqueous suspension vehicle has a viscosity (at 25° C.) of less than about 20 centipoise (cP), optionally less than about 10 cP, and, in one embodiment, less than about 5 cP. Examples of non-aqueous suspension vehicles herein include the vehicles in the Table 1 below:

TABLE 1

Exemplary Non-Aqueous Suspension Vehicles and Their Viscosity

| Vehicle | Viscosity (cP) |
|---|---|
| Ethanol | 1.3 (25° C.) |
| Dimethyl sulfoxide | 2.0 (20° C.) |
| N-methyl-2-pyrrolidone | 1.66 (25° C.) |
| Acetone | 0.33 (20° C.) |
| Benzyl benzoate | 9 (25° C.) |
| Tetrahydrofurfuryl alcohol | 6.2 (25° C.) |
| dimethyl ether of diethylene glycol (Diglym) | 1.2 (15° C.) |
| Ethyl lactate | 2 (20° C.) |
| Ethyl oleate | 7.4 (20° C.) |
| Isopropyl Myristate | 5.7 (20° C.) |
| Propylene glycol dicaprylate/dicaprate (MIGLYOL 840 ®) | 9 (25° C.) |

"Viscosity" refers to the measure of the resistance of a fluid which is being deformed by either shear stress or tensile stress; it can be evaluated using a viscometer or rheometer. Unless indicated otherwise, the viscosity measurement (centipoise, cP) is that at about 25° C. Viscosity as used herein can refer to that of either the non-aqueous suspension vehicle per se or that of the suspension formulation.

"Injectability" refers to the ease with which the suspension formulation can be administered to a subject. According to one embodiment of the invention, the injectibility of a given suspension formulation can be superior to the injectability of a liquid formulation comprising the same monoclonal antibody concentration and the same excipient(s) and concentration(s) thereof. In one embodiment, injectability refers to the injection glide force.

"Injection glide force" as used herein refers to the force required for the injection of a solution at a given injection rate via a needle of predetermined gauge and length. In one embodiment, it is evaluated using pre-filled syringe (e.g. 1.0 mL-long syringe with ≤25 gauge needle, or preferably ≤27 gauge needle) with glide force analyzed and established as a function of the distance of the plunger rod travelling inside the syringe at a steady compression rate (e.g. using "Syringe Glide Force Measurement" as in the Example herein). Time and force required for a manual injection (or time required for an injection using an autoinjector) may impact the usability of the product by the end-user (and thus compliance with the intended use of the product). In one embodiment, the Hagen-Poiseuille equation is utilized to estimate the travel (or glide) force (Equation 1).

$$F = \frac{8Q\mu L}{\pi R^6} \times A \quad \text{(Equation 1)}$$

Q=Volumetric flow rate
μ=Fluid viscosity
L=Needle length
R=Needle inner diameter
A=Cross sectional area of syringe plunger
F=Frictionless travel force According to Equation 1, the glide force is dependent on a number of parameters. The only parameter a formulation scientist can influence is viscosity. All other parameters (needle inner diameter, needle length, and cross sectional area of syringe plunger) are determined by the pre-fillable syringe itself. Formulations with a high viscosity can lead to high injection forces and long injection times since both parameters are proportional to viscosity. Generally accepted limits for injection force and injection time may depend e.g. on the indication and the dexterity of the patient population. In an embodiment exemplified herein, the parameters in Equation 1 were:

Q=Volumetric flow rate=0.1 mL/second
μ=Fluid viscosity=20 centipoise
L=Needle length=1.25 cm
R=Needle inner diameter=0.0105 cm (27 gauge needle)
A=Cross sectional area of syringe plunger=0.00316 cm$^2$
F=Frictionless travel force=16.6×10$^5$ dyne=16.6 newton In one embodiment, injection glide force is determined as a function of monoclonal antibody concentration by injecting 1-mL of suspension formulation using a 1-mL long syringe through a 27-gauge thin walled (TW) staked needle in 10 seconds.

In one embodiment the injection glide force of the suspension formulation is about 20 newtons or less.

In one embodiment the injection glide force of the suspension formulation is about 15 newton or less.

In one embodiment the injection glide force is from about 2 newton to about 20 newton.

In one embodiment the injection glide force is from about 2 newton to about 15 newton.

In one embodiment the injection glide force is less than about 20 newton.

In one embodiment the injection glide force is less than about 15 newton.

As used herein. "buffer" refers to a buffered solution that resists changes in pH by the action of its acid-base conjugate components. The buffer of this invention (if used) generally has a pH from about 4.0 to about 8.0, for example from about 5.0 to about 7.0, e.g. from about 5.8 to about 6.2, and in one embodiment its pH is about 6.0. Examples of buffers that will control the pH in this range include acetate, succinate, succinate, gluconate, histidine, citrate, glycylglycine and other organic acid buffers. In one embodiment herein, the buffer is a histidine buffer. A buffer is generally included in the pre-spray dried preparation and may be present in the suspension formulation prepared therefrom (but is not required therein).

A "histidine buffer" is a buffer comprising histidine ions. Examples of histidine buffers include histidine chloride, histidine acetate, histidine phosphate, histidine sulfate. In one embodiment, the histidine buffer is histidine-acetate or histidine-HCl. In one embodiment, the histidine buffer is at pH 5.5 to 6.5, optionally pH 5.8 to 6.2, e.g. pH 6.0.

The term "excipient" refers to an agent that may be added to a preparation or formulation, for example: as a stabilizer, to achieve a desired consistency (e.g., altering the bulk properties), and/or to adjust osmolality. Examples of excipients herein include, but are not limited to, stabilizers, sugars, polyols, amino acids, surfactants, chelating agents, and polymers.

A "stabilizer" herein is an excipient, or mixture of two or more excipients, which stabilizes a pharmaceutical formulation. For example, the stabilizer can prevent instability due to spray drying at elevated temperature. Exemplary stabilizers herein include saccharides, surfactants, and amino acids.

A "saccharide" herein comprises the general composition (CH2O)n and derivatives thereof, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, etc. The preferred saccharide herein is a nonreducing disaccharide, such as trehalose or sucrose.

Herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, New Jersey); polyethyl glycol, polypropyl glycol, and copolymers of ethylene and propylenic glycol (e.g. Pluronics, PF68 etc); etc. In one embodiment, the surfactant is polysorbate 20 or polysorbate 80. The surfactant may be included to prevent or reduce aggregation or denaturation of the monoclonal antibody in the preparation and/or formulation.

The term "amino acid" as used herein denotes a pharmaceutically acceptable organic molecule possessing an amino moiety located at α-position to a carboxylic group. Examples of amino acids include: arginine, glycine, ornithine, lysine, histidine, glutamic acid, asparagic acid, isoleucine, leucine, alanine, phenylalanine, tyrosine, tryptophane, methionine, serine, and proline. The amino acid employed is optionally in the L-form. Examples of amino acids which can be included as stabilizers in the preparations and/or formulations herein include: histidine, arginine, glycine, and/or alanine.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example. Specific examples of monoclonal antibodies herein include chimeric antibodies, humanized antibodies, and human antibodies.

A "spray dried" monoclonal antibody has been subjected to spray drying. The term includes the spray dried monoclonal antibody in powder form (i.e. prior to suspension) and in liquid form (i.e. when suspended in the non-aqueous suspension vehicle to form the suspension formulation).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, so long as they exhibit the desired biological activity (U.S. Pat. No. 4,816,567; Morrison et al., *Proc. Natl. Acad. Sri. USA*, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780). An example of a chimeric antibody herein is rituximab.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). Exemplary humanized antibodies herein include trastuzumab and bevacizumab.

A "human antibody" herein is one comprising an amino acid sequence structure that corresponds with the amino acid sequence structure of an antibody obtainable from a human B-cell. Such antibodies can be identified or made by a variety of techniques, including, but not limited to: production by transgenic animals (e.g., mice) that are capable, upon immunization, of producing human antibodies in the absence of endogenous immunoglobulin production (see, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807)); selection from phage display libraries expressing human antibodies (see, for example, McCafferty et al., *Nature* 348:552-553 (1990); Johnson et al., *Current Opinion in Structural Biology* 3:564-571 (1993); Clackson et al., *Nature,* 352:624-628 (1991); Marks et al., *J. Mol. Biol.* 222:581-597 (1991); Griffith et al., *EMBO J.* 12:725-734 (1993); U.S. Pat. Nos. 5,565,332 and 5,573,905); generation via in vitro activated B cells (see U.S. Pat. Nos. 5,567,610 and 5,229,275); and isolation from human antibody producing hybridomas. An example of a human antibody herein is ofatumumab.

A "multispecific antibody" herein is an antibody having binding specificities for two or more different epitopes.

A "bispecific antibody" is an antibody with binding specificities for two different epitopes. An example of a bispecific antibody specifically contemplated herein is HER3/EGFR Dual Acting Fab (DAF) molecule, such as DL1 if comprising human IgG1 heavy chains (US 2010/0255010; WO2010/108127).

Antibodies herein include "amino acid sequence variants" with altered antigen-binding or biological activity. Examples of such amino acid alterations include antibodies with enhanced affinity for antigen (e.g. "affinity matured" antibodies), and antibodies with altered Fc region e.g. with altered (increased or diminished) antibody dependent cellular cytotoxicity (ADCC) and/or complement dependent cytotoxicity (CDC) (see, for example, WO 00/42072, Presta, L. and WO 99/51642, Iduosogie et al.); and/or increased or diminished serum half-life (see, for example, WO00/42072, Presta, L.).

An "affinity matured variant" has one or more substituted hypervariable region residues of a parent antibody (e.g. of a parent chimeric, humanized, or human antibody) which improve binding of the affinity matured variant.

The antibody herein may be conjugated with a "heterologous molecule" for example to increase half-life or stability or otherwise improve the antibody. For example, the antibody may be linked to one of a variety of non-proteinaceous polymers, e.g., polyethylene glycol (PEG), polypropylene glycol, polyoxyalkylenes, or copolymers of polyethylene glycol and polypropylene glycol.

The antibody herein may be a "glycosylation variant" such that any carbohydrate attached to its Fc region is altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) describing antibodies with modified glycosylation.

The term "hypervariable region" when used herein refers to the amino acid residues of an antibody that are responsible for antigen binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, MD. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined. The CDRs of rituximab, bevacizumab, and trastuzumab are disclosed in FIGS. 8A-1, 8A-2, 8B, 9A-B, and 10A-B, respectively.

A "full length antibody" is one which comprises an antigen-binding variable region as well as a light chain constant domain (CL) and heavy chain constant domains, CH1, CH2 and CH3. The constant domains may be native sequence constant domains (e.g. human native sequence constant domains) or amino acid sequence variants thereof. Preferably, the full length antibody has one or more effector functions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991. Rituximab, trastuzumab, and bevacizumab are examples of full length antibodies.

A "naked antibody" is a monoclonal antibody that is not conjugated to a heterologous molecule, such as a cytotoxic moiety, polymer, or radiolabel. Rituximab, trastuzumab, and bevacizumab are examples of naked antibodies.

Antibody "effector functions" refer to those biological activities attributable to the Fc region (a native sequence Fc region or amino acid sequence variant Fc region) of an antibody. Examples of antibody effector functions include C1q binding, complement dependent cytotoxicity (CDC), Fc receptor binding, antibody-dependent cell-mediated cytotoxicity (ADCC), etc.

Depending on the amino acid sequence of the constant domain of their heavy chains, full length antibodies can be assigned to different classes. There are five major classes of full length antibodies: IgA, IgD, IgB, IgG, and IgM, and several of these may be further divided into "subclasses" (isotypes), e.g., IgG1, IgG2, IgG3, IgG4, IgA, and IgA2. The heavy chain constant domains that correspond to the different classes of antibodies are called alpha, delta, epsilon, gamma, and mu, respectively. The subunit structures and three-dimensional configurations of different classes of immunoglobulins are well known. The antibody herein is a human IgG1 according to one embodiment of the invention.

A "human IgG1" antibody herein refers to full length antibody comprising human IgG1 heavy chain constant domains.

The term "recombinant antibody" as used herein, refers to a monoclonal antibody (e.g. a chimeric, humanized, or human monoclonal antibody) that is expressed by a recombinant host cell comprising nucleic acid encoding the monoclonal antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia coli* cells or *Bacillus subtilis* cells, etc.

As used herein, "specifically binding" or "binds specifically to" refers to an antibody selectively or preferentially binding to an antigen. Preferably the binding affinity for antigen is of Kd value of $10^{-9}$ mol/l or lower (e.g. $10^{-10}$ mol/l), preferably with a Kd value of $10^{-10}$ mol/l or lower (e.g. $10^{-12}$ mol/l). The binding affinity is determined with a standard binding assay, such as surface plasmon resonance technique (BIACORE®).

A "therapeutic monoclonal antibody" is a monoclonal antibody used for therapy of a human subject. Therapeutic monoclonal antibodies disclosed herein include: CD20 antibodies for therapy of B cell malignancies (such as non-Hodgkin's lymphoma or chronic lymphocytic leukemia) or autoimmune diseases (such as rheumatoid arthritis and vasculitis); HER2 antibodies for cancer (such as breast cancer or gastric cancer); VEGF antibodies for treating cancer, age-related macular degeneration, macular edema, etc.

For the purposes herein, "rituximab" refers to an antibody comprising the variable heavy amino acid sequence in SEQ ID No. 3 and variable light amino acid in SEQ ID No. 4, and, optionally, the heavy chain amino acid sequence in SEQ ID No. 1 and light chain amino acid sequence in SEQ ID No. 2. This term specifically includes biosimilar rituximab.

For the purposes herein, "bevacizumab" refers to an antibody comprising the variable heavy amino acid sequence in SEQ ID No. 13 and variable light amino acid in SEQ ID No. 14, and, optionally, the heavy chain amino acid sequence in SEQ ID No. 11 and light chain amino acid sequence in SEQ ID No. 12. This term specifically includes biosimilar bevacizumab.

For the purposes herein, "trastuzumab" refers to an antibody comprising the variable heavy amino acid sequence in SEQ ID No. 23 and variable light amino acid in SEQ ID No. 24, and, optionally, the heavy chain amino acid sequence in SEQ ID No. 21 and light chain amino acid sequence in SEQ ID No. 22. This term specifically includes biosimilar trastuzumab.

The monoclonal antibody which is formulated herein is preferably essentially pure and desirably essentially homogeneous (i.e. free from contaminating proteins etc). "Essentially pure" antibody means a composition comprising at least about 90% by weight of the antibody, based on total weight of the composition, preferably at least about 95% by weight. "Essentially homogeneous" antibody means a composition comprising at least about 99% by weight of antibody, based on total weight of the composition.

II. Monoclonal Antibodies to be Formulated Herein

Exemplary techniques for producing monoclonal antibodies which can be formulated according to the present invention follow. In one embodiment, the antigen to which the antibody binds is a biologically important protein and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-b1, TGF-b2, TGF-b3, TGF-b4, or TGF-b5; a tumor necrosis factor (TNF) such as TNF-alpha or TNF-beta; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20, CD22 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1, IL-2, IL-3, IL-4, IL-5, IL-6, IL-7, TL-8. TL-9 and TI-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Exemplary molecular targets for antibodies encompassed by the present invention include CD proteins such as CD3, CD4, CD8, CD19, CD20, CD22, CD34 and CD40; members of the ErbB receptor family such as the EGF receptor, HER2, HER3 or HER4 receptor; B cell surface antigens, such as CD20 or BR3; a member of the tumor necrosis receptor superfamily, including DR5; prostate stem cell antigen (PSCA); cell adhesion molecules such as LFA-1, Mac 1, p150.95, VLA-4, ICAM-1. VCAM, alpha4/beta7 integrin, and alphav/beta3 integrin including either alpha or beta subunits thereof (e.g. anti-CD11a, anti-CD18 or anti-CD11b antibodies); growth factors such as VEGF as well as receptors therefor; tissue factor (TF); a tumor necrosis factor (TNF) such as TNF-alpha or TNF-beta, alpha interferon (alpha-IFN); an interleukin, such as IL-8; IgE; blood group antigens; flk2/flt3 receptor; obesity (OB) receptor; mpl receptor; CTLA-4; protein C etc.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

Exemplary antibodies which can be formulated according to the present invention include, but are not limited to the following: anti-ErbB antibodies, including anti-HER2 antibodies (e.g. trastuzumab or pertuzumab); antibodies that bind to a B-cell surface marker, such as CD20 (for example rituximab and humanized 2H7/ocrelizumab), CD22, CD40 or BR3; antibodies that bind to IgE, including omalizumab (XOLAIR®) commercially available from Genentech, E26, HAE1, IgE antibody with an amino acid substitution at position 265 of an Fc region thereof (US 2004/0191244 A1), Hu-901, an IgE antibody as in WO2004/070011, or antibody that binds the small extracellular segment on IgE, M1' (e.g. 47H4v5; see U.S. Pat. No. 8,071,097), see, also, Presta et al., *J. Immunol.* 151:2623-2632 (1993); International Publication No. WO 95/19181; U.S. Pat. No. 5,714,338, issued Feb. 3, 1998; U.S. Pat. No. 5,091,313, issued Feb. 25, 1992; WO 93/04173 published Mar. 4, 1993; WO 99/01556 published Jan. 14, 1999; and U.S. Pat. No. 5,714,338; antibodies that bind to vascular endothelial growth factor (VEGF) (e.g. bevacizumab) or a VEGF receptor; anti-IL-8 antibodies (St John et al., *Chest,* 103:932 (1993), and International Publication No. WO 95/23865); anti-PSCA antibodies (WO01/40309); anti-CD40 antibodies, including S2C6 and humanized variants thereof (WO00/75348); anti-CD11a antibodies, including efalizumab (RAPTIVA®) (U.S. Pat. No. 5,622,700, WO 98/23761. Steppe et al., *Transplant Intl.* 4:3-7 (1991), and Hourmant et al., *Transplantation* 58:377-380 (1994)); anti-CD18 antibodies (U.S. Pat. No. 5,622,700, issued Apr. 22, 1997, or as in WO 97/26912, published Jul. 31, 1997); anti-Apo-2 receptor antibody (WO 98/51793 published Nov. 19, 1998); anti-TNF-alpha antibodies including cA2 (REMICADE®) and adalimumab (HUMIRA®), CDP571 and MAK-195 (Afelimomub) (See, U.S. Pat. No. 5,672,347 issued Sep. 30, 1997, Lorenz et al. *J. Immunol.* 156(4):1646-1653 (1996), and Dhainaut et al. *Crit. Care Med.* 23(9):1461-1469 (1995)); anti-Tissue Factor (TF) (European Patent No. 0 420 937 B1 granted Nov. 9, 1994); anti-human $\alpha 4\beta_7$ integrin (WO 98/06248 published Feb. 19, 1998); anti-EGFR antibodies, including chimerized or humanized 225 antibody as in WO 96/40210 published Dec. 19, 1996; anti-CD3 antibodies, such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. *Arthritis Rheum* 39(1):52-56 (1996)); anti-CD52 antibodies such as alemtuzumab (CAMPATH-1H®) (Riechmann et al. *Nature* 332:323-337 (1988); anti-Fc receptor antibodies such as the M22 antibody directed against FcγRI as in Graziano et al. *J. Immunol.* 155(10): 4996-5002 (1995); anti-carcinoembryonic antigen (CEA) antibodies such as hMN-14 (Sharkey et al. *Cancer Res.* 55(23Suppl): 5935s-5945s (1995); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J. Immunol.* 26(1):1-9 (1996)); anti-CD38 antibodies, e.g. AT 13/5 (Ellis et al. *J. Immunol.* 155(2):925-937 (1995)); anti-CD33 antibodies such as Hu M195 (Jurcic et al. *Cancer Res* 55(23

Suppl):5908s-5910s (1995) and CMA-676 or CDP771; anti-CD22 antibodies such as LL2 or LymphoCide (Juweid et al. *Cancer Res* 55(23 Suppl):5899s-5907s (1995); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody Ova-Rex; anti-idiotypic GD3 epitope antibody BEC2; anti-αvβ3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1); anti-CCR5 (PRO 140); ABT-325; ABT-308; ABT-147; anti-beta7 (etrolizumab); anti-HER3/EGFR DAF (DL11f); anti-interleukin 6 receptor (IL6R) such as tocilizumab (ACTEMRA®); and anti-Abeta (see WO2003/070760 and WO2008/011348), etc.

In one embodiment the antibody which is formulated herein binds CD20 and is selected from: rituximab, ocrelizumab/humanized 2H7 (Genentech), ofatumumab (WO 04/035607, Genmab, Denmark), framework patched/humanized 1F5 (WO03/002607, Leung, S.), AME-133 (Applied Molecular Evolution), and humanized A20 antibody (US 2003/0219433, Immunomedics).

In one embodiment the antibody which is formulated binds HER2 and is trastuzumab or pertuzumab.

In one embodiment the antibody which is formulated binds VEGF and is bevacizumab.

In one embodiment the antibody that is formulated herein is a humanized antibody.

In one embodiment the antibody that is formulated is a recombinant antibody.

In one embodiment the antibody that is formulated has been expressed by a recombinant Chinese Hamster Ovary (CHO) cell.

In one embodiment the antibody that is formulated is a full length antibody.

In one embodiment the antibody that is formulated is a full length human IgG1 antibody.

In one embodiment the antibody that is formulated is a full length humanized IgG1 antibody.

In one embodiment the antibody that is formulated is a full length recombinant humanized IgG1 antibody.

In one embodiment the antibody that is formulated is a full length humanized IgG1 antibody that has been expressed by a recombinant Chinese Hamster Ovary (CHO) cell.

In one embodiment the antibody that is formulated binds an antigen selected from: CD20 (e.g. rituximab), HER2 (e.g. trastuzumab), VEGF (bevacizumab), IL6R (tocilizumab), beta7 (etrolizumab). Abeta, HER3 and EGFR (DL11f), and M1' (47H4v5).

In one embodiment the antibody formulated is rituximab.

In one embodiment the antibody formulated is trastuzumab.

In one embodiment the antibody formulated is bevacizumab.

III. The Pre-Spray Dried Preparation

A preparation of the monoclonal antibody is generally prepared which is to be subjected to spray drying, the so-called "pre-spray dried preparation" herein.

In one embodiment, the pre-spray dried preparation comprises a monoclonal antibody preparation which has been subjected to one or more prior purification steps, such as affinity chromatography (e.g. protein A chromatography), hydrophobic interaction chromatography, ion exchange chromatography (anion and/or cation exchange chromatography), virus filtration, etc. Thus, the antibody preparation may be purified, essentially pure, and/or essentially homogeneous.

In one embodiment, the monoclonal antibody in the pre-spray dried preparation is concentrated. Exemplary methods for concentrating the antibody include filtration (such as tangential flow filtration or ultrafiltration), dialysis etc.

The pre-spray dried preparation may be liquid or frozen.

The pH of the pre-spray dried preparation is optionally adjusted by a buffer. The buffer may for example have a pH from about 4 to about 8, e.g. from about 5 to 7, for example 5.8 to 6.2, and, in one embodiment, is approximately 6.0. A histidine buffer is an exemplified embodiment herein. The concentration of the buffer is dictated, at least in part, by the desired pH. Exemplary concentrations for the buffer are from about 1 mM to about 200 mM, or from about 10 mM to about 40 mM.

The pre-spray dried preparation optionally also comprises one or more stabilizers which prevent denaturation and/or aggregation of the antibody during the spray drying process. Examples of such stabilizers include saccharides (e.g. sucrose or trehalose) and/or surfactants (e.g. polysorbate 20 or polysorbate 80) and/or amino acids (e.g. histidine, arginine, glycine, and/or alanine). The stabilizers are generally added in amount(s) which protect and/or stabilize the monoclonal antibody at the lowest amount of stabilizer possible, to avoid increasing the viscosity of the final formulation.

With respect to saccharide stabilizers, such as disaccharides (e.g. trehalose or sucrose), the molar ratio of saccharide: monoclonal antibody (or disaccharide: monoclonal antibody) is optionally from about 50 to about 400:1, e.g. from about 100 to about 250:1. Stated differently, exemplary saccharide concentrations in the pre-spray dried preparation are, for example, from about 10 mM to about 1M, for example from about 50 mM to about 300 mM.

With respect to surfactant (if included in the pre-spray drying formulation), polysorbate 20 or polysorbate 80 are examples of surfactants that can be included. The surfactant is generally included in an amount which reduces or prevents denaturation and/or aggregation of the monoclonal antibody during the spray drying process. The surfactant (e.g. polysorbate 20 or polysorbate 80) concentration is optionally from about 0.0001% to about 1.0%, for example from about 0.01% to about 0.1%.

The pre-spray dried preparation may be subjected to spray drying procedures such as those described in the following section.

IV. Spray Drying the Preparation

Spray drying herein is distinct from freeze drying commonly used to prepare monoclonal antibody formulations insofar as it is performed at temperatures above ambient temperature. Spray drying temperatures are commonly expressed as "air inlet" and "air outlet" temperatures. In one embodiment, the spray drying is performed at an air inlet temperature from about 100° C. to about 220° C. (for example from about 120° C. to about 160° C.) and an air outlet temperature from about 50° C. to about 100° C. (for example from about 60° C. to about 80° C.).

The spray drying process generally comprises: atomization of the liquid feed; drying of the droplets; and separation or recovery of the dried product.

Embodiments of atomizers herein include: rotary atomizers, pneumatic nozzle atomizers, ultrasonic nozzle atomizers, sonic nozzles, etc.

The contact between the liquid feed and the drying air can occur in two different modes. In a co-current system, drying air and particles (droplets) move through the drying chamber in the same direction. When drying air and droplets move in an opposite direction, this is called a counter-current mode. Particles produced in counter-current mode usually show a higher temperature than the exhausting air. The exhausted air itself can leave the system or can be recirculated. By choosing from the various spray dryer designs (size, atomizer, aseptic conditions, etc.) and adjusting the different process parameters (drying air flow, drying air temperature, etc.), the final powder properties like particle size, shape and structure or even sterility can be modified. If the resulting moisture of the recovered powder is not sufficiently low, post-treatment might be required, e.g., in the form of fluid bed dryers and coolers, contact dryers or even microwave dryers.

When the liquid feed is atomized, its surface to mass ratio is increased, the heat transfer between the air and the droplets is accelerated, and droplets can dry relatively rapidly. Two convection processes may be involved: heat transfer (air to droplet) and mass transfer of moisture (droplet to air). In the latter, moisture permeates through the boundary layer that surrounds each droplet. Transfer rates may be influenced by temperature, humidity, transport properties of the surrounding air, droplet diameter and relative velocity between droplet and air.

The last step of a spray drying process is typically the separation of the powder from the air/gas and the removal of the dried product. In some embodiments, this step is as effective as possible to obtain high powder yields and to prevent air pollution through powder emission to the atmosphere. To this end, various methods are available such as cyclones, bag filters, electrostatic precipitators, high pressure gas, electrostatic charge and combinations thereof.

The spray drying process produces particles comprising the monoclonal antibody.

In one embodiment, the characteristics of the spray dried powder comprise any one or more or the following:

(a) average particle size: from about 2 microns to about 30 microns; e.g. from about 2 microns to about 10 microns;
(b) particle morphology: predominantly spherical particles, some dimples or holes in particles, "dry raisin" shape;
(c) water content: less than about 10%, for example less than about 5%, e.g., where water content is measured by a chemical titration method (e.g. Karl Fischer method) or a weight-loss method (high-temperature heating); and
(d) stability: e.g., assessed by suspending the particles in a vehicle and evaluating physical stability and/or chemical stability and/or biological activity of the suspension preparation. In one embodiment, the percentage monomer of such preparation is 95% to 100%, e.g. as evaluated by size exclusion chromatography (SEC).

V. The Suspension Formulation

The spray dried monoclonal antibody particles prepared as described in the preceding section are combined with a non-aqueous suspension vehicle to generate the suspension formulation. This formulation is suitable for administration to a subject. Generally, the suspension formulation will not be subjected to either prior, or subsequent, lyophilization or crystallization. In one embodiment, a subcutaneous administration device (e.g. a pre-filled syringe) is filled with the suspension formulation and used for administering the formulation (see below for more detailed disclosure regarding devices and methods of treatment).

The invention also provides a method of making a suspension formulation comprising suspending the spray dried monoclonal antibody in a non-aqueous suspension vehicle.

In one embodiment the antibody concentration in the suspension formulation is about 200 mg/mL or more.

In one embodiment the antibody concentration in the suspension formulation is from about 200 mg/mL, to about 500 mg/mL.

In one embodiment the antibody concentration in the suspension formulation is from about 250 mg/mL to about 400 mg/mL.

In one embodiment the antibody concentration in the suspension formulation is from about about 250 mg/mL to about 350 mg/mL.

The non-aqueous suspension vehicle preferably has a viscosity at 25° C., which is less than about 20 centipoise, for example, less than about 10 centipoise, and optionally less than than about 5 centipoise.

According to one embodiment of the invention, the viscosity of the suspension formulation is from about 5 to about 100 centipoise, for instance, from about 10 to about 70 centipoise at 25° C. In one embodiment, viscosity of the suspension formulation is measured using a cone and plate rheometer (e.g. a AR-G2 TA Instrument rheometer).

In one embodiment, the average particle size in the suspension formulation is from about 2 microns to about 30 microns, for example from about 5 microns to about 10 microns.

In one embodiment, the suspension formulation has an injection glide force of less than about 20 newton, for example less than about about 15 newton. Such injection glide force may be determined as a function of monoclonal antibody concentration by injecting 1-mL suspension using a 1-mL long syringe through a 27-gauge TW staked needle in 10 seconds.

In one embodiment the non-aqueous suspension vehicle is selected from: propylene glycol dicarprylate/dicaprate, benzyl benzoate, ethyl lactate, or mixtures of two or three thereof.

In one embodiment the non-aqueous suspension vehicle comprises ethyl lactate.

In one embodiment, the non-aqueous suspension vehicle comprises a mixture of at least two non-aqueous suspension vehicles: Vehicle A plus Vehicle B, wherein the viscosity of Vehicle A is less than that of Vehicle B, but the monoclonal antibody stability in Vehicle B is greater than that in Vehicle A. An embodiment of such mixture is exemplified by the mixture of ethyl lactate and propylene glycol dicarprylate/dicaprate (for example).

In one aspect, the suspension formulation comprises a spray dried full length human IgG1 monoclonal antibody at a concentration from about 200 mg/mL to about 400 mg/mL suspended in a non-aqueous suspension vehicle with a viscosity less than about 20 centipoise, wherein the formulation has an average particle size from about 2 microns to about 10 microns, and injection glide force less than about 15 newton.

The suspension formulation optionally further comprises one or more excipients or stabilizers. Examples of such stabilizers include saccharides (e.g. sucrose or trehalose) and/or surfactants (e.g. polysorbate 20 or polysorbate 80) and/or amino acids (e.g. histidine, arginine, glycine, and/or alanine). The stabilizers are generally present in an amount which protects and/or stabilizes the monoclonal antibody at the lowest amount of stabilizer possible, to avoid increasing the viscosity of the suspension formulation. In one embodiment, the stabilizers are present in the suspension formulation as a result of having been added to the pre-spray dried preparation, and/or have been added to the suspension formulation, as desired.

With respect to saccharide stabilizers, such as disaccharides (e.g. trehalose or sucrose), the molar ratio of saccharide: monoclonal antibody (or disaccharide: monoclonal antibody) in the suspension formulation is optionally from about 50 to about 400:1, e.g. from about 100 to about 250:1. Stated differently, exemplary saccharide concentrations in the suspension formulation are from about 10 mM to about 1 M, for example from about 50 mM to about 300 mM.

With respect to surfactant (if included in the pre-spray dried preparation), polysorbate 20 or polysorbate 80 are examples of surfactants which can be present in the suspension formulation. The surfactant (e.g. polysorbate 20 or polysorbate 80) concentration is optionally from about 0.0001% to about 1.0%, for example from about 0.01% to about 0.1%.

The suspension formulation is generally sterile, and this can be achieved according to the procedures known to the skilled person for generating sterile pharmaceutical formulations suitable for administration to human subjects, including filtration through sterile filtration membranes, prior to, or following, preparation of the suspension formulation.

Moreover, the formulation is desirably one which has been demonstrated to be stable upon storage. Various stability assays are available to the skilled practitioner for confirming the stability of the formulation. Stability can be tested by evaluating physical stability, chemical stability, and/or biological activity of the antibody in the suspension formulation around the time of formulation as well as following storage at different temperatures and time-points. In one embodiment, monoclonal antibody stability is assessed by size distribution (percentage monomer, aggregation, and/or fragmentation) before and after spray drying (e.g. before and after spray drying over 3-month storage under the accelerated temperature of 40° C.). In one embodiment, size distribution is assessed using using size exclusion chromatography-high performance liquid chromatography (SEC-HPLC). In one embodiment, the percentage monomer loss in the suspension formulation (as measured by SEC-HPLC) over 3 months is less than about 10%, for example less than about 5%.

In one embodiment, the invention provides a method of making a pharmaceutical formulation comprising preparing the suspension formulation as described herein, and evaluating any one or more of the following properties of the formulation:
(a) physical stability, chemical stability, and/or biological activity of the monoclonal antibody in the suspension (e.g. measuring percentage monomer using size exclusion chromatography);
(b) viscosity of the suspension formulation;
(c) injectability or injection glide force of the suspension formulation;
(d) surface energy analysis (SEA) or heat of sorption, e.g. by inverse gas chromatography (IGC) to evaluate particle-suspension vehicle interaction;
(e) particle size (e.g. average and/or peak particle size, e.g. by laser diffraction analyzer); and/or
(e) suspension physical stability (settling, homogeneity over time, particle sedimentation rate, etc).

Further detail of exemplary assays for these properties is provided in the example below.

One or more additional other pharmaceutically acceptable carriers, excipients or stabilizers such as those described in *Remington's Pharmaceutical Sciences* 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as BDTA; metal complexes (e.g. Zn-protein complexes); biodegradable polymers such as polyesters; preservatives; and/or salt-forming counterions such as sodium.

VI. Medicaments and Treatments Using the Suspension Formulation

In one embodiment, the invention provides a method of treating a disease or disorder in a subject comprising administering the suspension formulation described herein to a subject in an amount effective to treat the disease or disorder.

Thus, the invention provides: the suspension formulation as described herein for treating a patient in need of treatment with the monoclonal antibody in the suspension formulation; and use of the suspension formulation in the preparation of a medicament for treating a patient in need of treatment with the monoclonal antibody in the suspension formulation. In an alternative embodiment, the invention provides: the formulation as described herein for treating a disease or disorder in a patient; and use of the formulation in the preparation of a medicament for treating a disease or disorder in a patient.

In addition, the invention provides a method of treating a patient comprising administering the formulation described herein to a patient in order to treat a disease or disorder in the subject. Preferably the formulation is administered subcutaneously to the subject or patient. In one embodiment, the formulation is administered by a pre-filled syringe containing the formulation therein.

Where the antibody in the formulation binds to HER2, the suspension formulation is preferably used to treat cancer. The cancer will generally comprise HER2-expressing cells, such that the HER2 antibody herein is able to bind to the cancer cells. Thus, the invention in this embodiment concerns a method for treating HER2-expressing cancer in a subject, comprising administering the HER2 antibody pharmaceutical formulation to the subject in an amount effective to treat the cancer. Exemplary cancers to be treated herein with a HER2 antibody (e.g. trastuzumab or pertuzumab) are HER2-positive breast cancer or gastric cancer.

Where the antibody in the formulation binds to a B-cell surface marker such as CD20, the formulation may be used to treat a B-cell malignancy, such as NHL or CLL, or an autoimmune disease (e.g. rheumatoid arthritis or vasculitis).

Where the antibody in the formulation binds VEGF (e.g. bevacizumab), the formulation may be used to inhibit angiogenesis, treat cancer (such as colorectal, non-small cell lung (NSCL), glioblastoma, breast cancer, and renal cell carcinoma), or treat age-related macular degeneration (AMD) or macular edema.

Where the indication is cancer, the patient may be treated with a combination of the suspension formulation, and a chemotherapeutic agent. The combined administration includes coadministration or concurrent administration, using separate formulations or a single pharmaceutical formulation, and consecutive administration in either order, wherein there is a time period when both (or all) active agents simultaneously exert their biological activities. Thus, the chemotherapeutic agent may be administered prior to, or following, administration of the composition. In this embodiment, the timing between at least one administration of the chemotherapeutic agent and at least one administration of the formulation is preferably approximately 1 month or less, and most preferably approximately 2 weeks or less. Alternatively, the chemotherapeutic agent and the formulation are administered concurrently to the patient, in a single formulation or separate formulations.

Treatment with the suspension formulation will result in an improvement in the signs or symptoms of the disease or disorder. Moreover, treatment with the combination of the chemotherapeutic agent and the antibody formulation may result in a synergistic, or greater than additive, therapeutic benefit to the patient.

The formulation is administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, or intrathecal administration.

Intramuscular or subcutaneous administration of antibody composition is preferred, with subcutaneous administration being most preferred.

For subcutaneous delivery, the formulation may be administered via syringe (e.g. pre-filled syringe); autoinjector; injection device (e.g. the INJECT-EASE™ and GEN-JECT™ device); injector pen (such as the GENPEN™); or other device suitable for administering a suspension formulation subcutaneously. The preferred device herein is a pre-filled syringe.

For the prevention or treatment of disease, the appropriate dosage of the monoclonal antibody will depend on the type of disease to be treated, as defined above, the severity and course of the disease, whether the monoclonal antibody is administered for preventive or therapeutic purposes, previous therapy, the patient's clinical history and response to the monoclonal antibody, and the discretion of the attending physician. The antibody is suitably administered to the patient at one time or over a series of treatments. Depending on the type and severity of the disease, about 1 µg/kg to 50 mg/kg (e.g. 0.1-20 mg/kg) of antibody is an initial candidate dosage for administration to the patient, whether, for example, by one or more separate administrations, or by continuous infusion. The dosage of the antibody will generally be from about 0.05 mg/kg to about 10 mg/kg. If a chemotherapeutic agent is administered, it is usually administered at dosages known therefor, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, MD (1992).

VII. Articles of Manufacture

The invention herein also concerns a device with the suspension formulation therein. Preferably the device is a subcutaneous administration device, such as a pre-filled syringe.

In a related aspect, the invention provides a method of making an article of manufacture comprising filling a container with the suspension formulation.

Embodiments of the container in the article of manufacture include: syringes (such as pre-filled syringe), autoinjectors, bottles, vials (e.g. dual chamber vials), and test tubes, etc. The container holds the suspension formulation and the label on, or associated with, the container may indicate directions for use. The article of manufacture may further include other materials desirable from a commercial and user standpoint, including other buffers, diluents, filters, needles, syringes, and package inserts with instructions for use as noted in the previous section.

The invention will be more fully understood by reference to the following examples. They should not, however, be construed as limiting the scope of the invention. All literature and patent citations are incorporated herein by reference.

EXAMPLES

Developing high-concentration monoclonal antibody liquid formulations (≥200 mg/mL) for subcutaneous (SC) administration is often challenging with increased viscosity that makes injection difficult. This investigation was intended to overcome this obstacle using a non-aqueous powder suspension approach. Three human IgG1 monoclonal antibodies were spray dried and suspended in a suspension vehicle at different monoclonal antibody concentrations. Propylene glycol dicaprylate/dicaprate, benzyl benzoate, and ethyl lactate were employed as model suspension vehicles. Suspensions were characterized for viscosity, particle size, and syringeability. Physical stability of the suspension was visually inspected. The suspensions in general outperformed the liquid solutions in terms of injectability despite higher viscosity at the same monoclonal antibody concentrations. Powder formulations and powder properties appeared to have little effect on suspension viscosity or injectability. Among the three suspension vehicles, ethyl lactate suspensions had the lowest viscosity, below 20 centipoise, and lowest syringe injection glide force, below 15 newton, at monoclonal antibody concentration as high as 333 mg/mL (total powder concentration at 500 mg/mL). Inverse gas chromatography (IGC) analysis of the suspension supported the conclusion that the suspension vehicle was the most important factor impacting suspension performance. Ethyl lactate rendered greater heat of sorption than other suspension vehicles. Without being bound by any one theory, this indicates that strong particle-suspension vehicle interaction may reduce particle-particle self association, leading to low suspension viscosity and glide force. Ethyl lactate suspensions, however, lacked the physical suspension stability exhibited by propylene glycol dicaprylate/dicaprate and benzyl benzoate. Specific mixtures of ethyl lactate and propylene glycol dicaprylate/dicaprate improved the overall suspension performance in high monoclonal antibody concentration suspensions.

Amongst other things, these examples demonstrated the viability of high monoclonal antibody concentration (>300 mg/mL) in suspension formulations for SC administration.

Materials and Methods

Three recombinant chimeric/humanized monoclonal antibodies of the human IgG1 subclass bevacizumab, trastuzumab and rituximab were manufactured by Genentech (South San Francisco, CA). These antibodies were expressed by Chinese hamster ovary (CHO) cell lines. All antibody drug substance liquid solutions were concentrated to 100 mg/ml using a tangential-flow filtration unit (PELLICON3® 10 kD, Millipore, Billerica, MA) and formulated with trehalose dihydrate. All bulks were buffered to a pH of ~6.0. For antibody powder suspension preparation, propylene glycol dicaprylate/dicaprate (Batch #091125, SASOL, Hamburg, Germany), benzyl benzoate (Cat #B9550, Sigma-Aldrich, St Louis, MO), and ethyl lactate (Lot #BCBC7752, Sigma-Aldrich, St. Louis, MO) were used as suspension vehicles.

Spray Drying

Two types of spray dryers were used in this study, a pilot-scale unit (MS-35, SPX Flow Technology Systems, Inc., Elkridge, MD) and a bench-top unit (B-191, Buchi Corp., New Castle, DE). MS-35 is approximately 2-fold larger capacity than B-191, i.e., 2.5 vs. 1.6 kg/hour of the maximum water evaporation rate and 35 vs. 20 kg/hour maximum compressed air consumption rate. The pilot-scale unit was constructed mostly of stainless steel with heat insulation (drying chamber, cyclone, etc.) while the bench-top unit was made of glass. The pilot scale unit was equipped with a high-efficiency cyclone. To calculate the yield of powder collection, only the powder collected in the receiver was considered for the pilot-scale unit, and the powder collected on the cyclone and the receiver lid was included for the bench-top unit. The spray drying conditions and the characteristics dry powders produced using both spray dryers are listed in Table 2.

Particle Size Analysis

The particle size distribution was measured using a laser diffraction analyzer (LA-950, Horiba Instruments, Kyoto, Japan). The LA-950 consists of two light sources (blue LAD, red laser), a sample handling system to control the interaction of particles and incident light, and an array of high quality photodiodes to detect the scattered light over a wide range of angles. The scattered light collected on the detectors was used to calculate the particle size distribution of the sample analyzed using the Mie Theory. For spray dried samples, several milligrams of the dry powders were dispersed in 50 mL of isopropyl alcohol in the MiniFlow cell attached on LA-950 and sonicated using the sonicator also attached on LA-950 for about one minutes prior to analysis. For particles suspended in vehicles were diluted with each vehicle in FractionCell and mix with a stirrer attached on LA-950 prior to analysis.

Density Analysis

The density of the powder was determined by mixing 500 mg of powder in 4 mL of propylene glycol dicaprylate/dicaprate oil in a volumetric cylinder and measuring the displaced oil volume as the powder volume. Powder density can be calculated using powder weight and volume.

Scanning Electron Microscopy

Surface morphology of spray dried samples was examined using an environmental scanning electron microscope (XL30, FEL, Hillsboro, OR). Each sample was mounted on aluminum stubs and sputter coated with 10 nm layer of AuPd, and scanned at a voltage of 2 kV, and the photographs were taken at magnifications of 1000 and 2000.

Water Content Analysis

Residual moisture in spray dried samples were determined using volumetric Karl Fischer titration analyzer (DL31, Mettler-Toledo). Approximately 100 mg of each sample was injected into the titration cell that contained

TABLE 2

Spray-drying conditions in two types of spray dryers and characterization results of three antibodies formulated with trehalose at 1:2 antibody:trehalose weight ratio

| | | Monoclonal Antibody Type | | | | | |
|---|---|---|---|---|---|---|---|
| | | Bevacizumab | | Trastuzumab | | Rituximab | |
| | Spray Dryer | Pilot | Bench-top | Pilot | Bench-top | Pilot | Bench-top |
| Drying Condition | Inlet Temp. (° C.) | 182 | 134 | 182 | 138 | 182 | 136 |
| | Outlet Temp. (° C.) | 87 | 88 | 87 | 89 | 87 | 88 |
| | Liq Feed Rate (mL/min) | 12 | 3 | 12 | 3 | 13 | 3 |
| | Liq Vol Dried (mL) | 250 | 50 | 250 | 50 | 250 | 50 |
| | Yield (%) | 99 | 60 | 100 | 65 | 98 | 59 |
| | Particle Size ($D_{50}$) (μm) | 9.6 | 2.5 | 8.8 | 2.8 | 10.6 | 5.1 |
| | Water Content (%) | 4.0 | 7.6 | 4.7 | 6.9 | 5.0 | 8.8 |

Freeze Drying

Monoclonal antibody solutions were also freeze-dried to compare the dry-state stability with spray dried samples. Liquid formulations were aliquoted in 1 mL into 2 cc glass vials placed with butyl stoppers, then placed on pre-chilled shelves at −50° C. in a lyophilizer (Model #LYOMAX2®, BOC Edward, Tewksbury, MA). The samples were dried by lowering the pressure to 100 mTorr and increasing the shelf temperature to −25° C. during the primary drying, followed by the secondary drying at 35° C. The total lyophylization cycle time was approximately 60 hours.

anhydrous methanol. Hydranal composite 2 volumetric reagent (Cat #34696, Hiedel-deHaen, Heidelberg, Germany) was used as a titrant.

Size Exclusion Chromatography

The quantitation of size variants was determined by size exclusion chromatography. This analysis utilized a G3000SW$_{XL}$ column, 7.8 mm ID×30 cm, 5 μm (TOSOH BioScience) run on an HPLC system (1100, Agilent). The mobile phases are 0.2 M potassium phosphate and 0.25 M potassium chloride at pH 6.2 for bevacizumab, 0.1 M potassium phosphate at pH 6.8 for trastuzumab, and 0.2 M potassium phosphate and 0.25 M potassium chloride at pH 7.0 for rituximab. The chromatography was run isocratically at a flow rate of 0.5 mL/min for 30 minutes. The column temperature was maintained at ambient for bevacizumab and rituximab, and 30° C. for trastuzumab, and the eluent absorbance was monitored at 280 nm. Each monoclonal antibody was diluted with its respective formulation buffer to 25 mg/mL for bevacizumab and 10 mg/mL for both trastuzumab and rituximab. Their injection volume is 10 µL for bevacizumab and for 20 µL for both trastuzumab and rituximab.

Monoclonal Antibody Physical Stability in Spray dried and Freeze-Dried Powder Formulations Spray dried and freeze-dried powder samples were aliquoted into 2 cc glass vial, approximately 25 monoclonal antibody. Each vial was sealed with a rubber stopper and FLIP-OFF® cap and stored at 40° C. for up to 3 months. At the stability time points of time zero (immediately after drying), 1, 2, 3 months, each dry sample was reconstituted with 1 mL of purified water, and the antibody physical stability was determined by protein size distribution (% monomer, aggregation, and fragmentation) using SEC-HPLC.

Preparation of Suspension Formulations

The powder was weighed onto a 2-mL vial. Based on the powder density determined, the appropriate amount of suspension vehicle was added to prepare the powder concentration in the unit of mg of powder in 1 mL of suspension volume. Samples were then homogenized for 2 minutes at 7500 rpm using a 0.5-cm tip probe on a Tempest Virtishear homogenizer (Virits Corp, Gardiner, NY).

Viscosity Measurement

The viscosity of solution and suspension samples was measured using a cone and plate rheometer (AR-G2 TA Instrument, New Castle, DE). Each sample was loaded onto the lower measuring plate and allowed to come to thermal equilibrium at 25° C. A solvent trap equipped on AR-G2 was used to prevent solution evaporation during the measurement. The sample viscosity was measured every 10 seconds for 2 minutes using a cone with a 20 mm diameter and 1 degree angle at shear rate of 1000 per second.

Syringe Glide Force Measurement

One mL of suspension was drawn into a 1.0 mL-Long 27G TW ½" staked needle syringe (BD, Franklin Lakes, NJ) sealed with a plunger stopper (W4023/FLT, West Pharmaceutical, Lionville, PA). The internal barrel of the syringe was coated with 0.5 mg silicone oil (Dow 360 Medical Fluid, 1.000 cSt). A Material Testing System (Model 5542, Instron, Grove City, PA) with a load cell was used to apply a steady compression rate of 190 mm/min. The gliding force profile was analyzed and established as a function of the distance of the plunger rod travelling inside the syringe barrel.

Inverse Gas Chromatography (IGC)

IGC experiment was performed using a Surface Energy Analysis (SEA) System (MSM-iGC 2000, Surface Measurement Services Ltd, Allentown, PA). Approximately 200 mg of powder sample was packed into individual silanised glass columns and both ends of columns were sealed using silanised glass wool to prevent sample movement. The specific surface areas of the powder samples were determined by measuring the Octane adsorption isotherms at 30° C. and 0% RH from the IGC SEA. The BET specific surface areas of the samples were subsequently calculated from their corresponding octane isotherms, within the partial pressure range (10% to 35% $P/P_0$). Decane, nonane, octane and heptane were used as alkane probes for dispersive surface energy determination. Specific acid-based Gibbs free energy was also measured using acetone, acetonitrile, ethanol and ethyl acetate. For heat of sorption measurement, the suspension vehicles were used as the gaseous probes. All samples were pre-conditioned in-situ with a carrier gas of helium at 30° C. for 2 hours, and all the measurements were conducted at 30° C. with a carrier gas flow rate of 10 $cm^3$/sec.

Results and Discussion

Spray Dried Antibody/Trehalose Powders

Three types of monoclonal antibodies were formulated in liquid solutions containing trehalose, serving as a carbohydrate stabilizer to monoclonal antibody, at the weight ratio of 1:2 of trehalose:antibody prior to spray drying. This low weight ratio is equivalent to approximately 220:1 molar ratio was used for the purpose of minimizing its volume contribution, which was below the minimum molar ratio of 300:1 commonly used for sugar to stabilize proteins as a lyoprotectant (Shire et al., *J Pharm Sci* 93:1390-1402 (2004)). Note that a 400 mg powder/mL suspension represents a 270 mg antibody/mL concentration even at the 1:2 weight ratio of trehalose:antibody, which was at the low limit of the target antibody concentration for this study.

Three monoclonal antibodies formulated at 100 mg/mL with 50 mg/mL trehalose, were spray dried using a benchtop spray dryer (B-191) and a pilot-scale spray dryer (MS-35). Spray-drying conditions and powder characterization results are summarized in Table 2. Comparable outlet temperatures of 87-89° C. were employed for all samples because outlet temperature was considered the key parameter dictating the spray-drying capability (Maa el al., *Pharm Dev Technol* 2:213-223 (1997); Lee G. Spray Drying of Proteins, in "Rational Protein Formulation: Theory and Practice" (Eds. Carpenter J, Manning M), Pharmaceutical Biotechnology Series (Ed. Borchardt R). Plenum Press, pp. 135-158 (2002); Maury et al. *Eur. J. Pharm. Biopharm.* 59:566-573 (2005); Maa et al. *Biotech. Bioeng.* 60:301-309 (1998); and Maa et al. *J. Pharm. Sci.* 87:152-159 (1998)). The pilot-scale spray dryer demonstrated better performance in powder collection yield (>96%) and water content of 4-5%, while the samples dried by the bench-top spray dryer had 60% yield and 7-9% water content. The pilot-scale dryer was also capable of producing larger particles of 8-11 µm ($D_{50}$) whereas the bench-top dryer produced 2-5 µm ($D_{50}$) particles. The advantages of the pilot-scale dryer can be attributed to efficient energy use and greater powder collection efficiency. Particle shape and morphology for all antibodies was generally spherical with dimples, which were antibody dependent. The type of the spray dryer did not affect particle morphology. Overall, dryer performance and the antibody type resulted in some degree of variations in particle properties. Although these variations are not dramatic, they allowed us to evaluate their effect on suspension performance.

Antibody Physical Stability in Spray dried and Freeze-Dried Powder Formulations

A general concern about spray drying of biologics was high temperature stress, particularly for the pilot dryer which had higher inlet temperature of >180° C. Antibody physical stability of the dry samples was determined upon reconstitution with purified water by protein size distribution (% monomer, aggregation and fragmentation) using SEC-HPLC before and after spray drying over 3-month storage under the accelerated temperature of 40° C. (FIG. 1). Despite the high drying temperature used in the pilot-scale spray dryer, the impact of the drying process on (%) monomer was minimal. The antibody physical stability for spray dried bevacizumab and trastuzumab was compared to the freeze-dried counterparts by monitoring the change in (%) monomer at 40° C. over 3 months. The (%) monomer for all samples decreased at the accelerated condition mainly due to aggregation, which is not surprising given the sub-optimal amount of trehalose to protect antibody in the formulation. However, the spray dried samples had greater antibody physical stability than the freeze-dried samples. The (%) monomer of spray dried trastuzumab and bevacizumab decreased by ~2% and ~4% respectively, whereas both freeze-dried antibodies suffered a greater (%) monomer loss of ~6.5% over 3 months, despite their lower water content of ~0.8%. Thus, spray drying is a viable approach, from the process and stability perspective, in making antibody powders for suspension formulation development.

Selection of Suspension Vehicles

The primary criterion for the selection of the suspension vehicle was low viscosity, preferably <10 Cp, as suspension vehicle viscosity would contribute to suspension viscosity in a linear fashion based on Einstein's Equation for the viscosity of solutions (Einstein, A., *Annalen der Physik* 34:591-92 (1911)).

$$\eta=\eta_o(1+2.5\varphi) \quad \text{(Equation 2)}$$

Where $\eta$ is the suspension viscosity. $\eta_o$ the viscosity of pure suspension vehicle, and $\varphi$ the volume fraction of the solute.

The three suspension vehicles selected for this study, propylene glycol dicaprylate/dicaprate, benzyl benzoate, and ethyl lactate, met this criterion (Table 3). MIGLYOL 840® is propylene glycol diesters of caprylic and capric acids from the MIGLYOL® neutral oil family. MIGLYOL 810® and MIGLYOL 812® have been approved for intravenous and intramuscular injections but they are viscous, >30 cp at ambient temperature. Propylene glycol dicaprylate/dicaprate, the least viscous in the family (~9 cp), has been used for transdermal applications (Mahjour et al., *Intl J Pharm* 95:161-169 (1999); Seniro, W., *Intl J Toxicol* 18:35-52 (1999)). Benzyl benzoate is similar to propylene glycol dicaprylate/dicaprate in viscosity, ~9 cp, and has often been used as a preservative in liquid injectables at <10% concentration. Ethyl lactate has been used commonly in pharmaceutical preparations, food additives, and fragrances due to its relatively low toxicity. Although ethyl lactate has not yet been parenterally approved, it had low toxicity in mice for intramuscular and intravenous injection (Spiegel and Noseworthy, *J Pharm Sci* 52:917-927 (1963); Mottu et al., *PDA J. Pharm. Sci. Technol.* 54:456-469 (2000)). Ethyl lactate has a water-like viscosity, ~2 cp.

Effect of Antibody Type and Powder Properties on Suspension Viscosity

Figure 2:
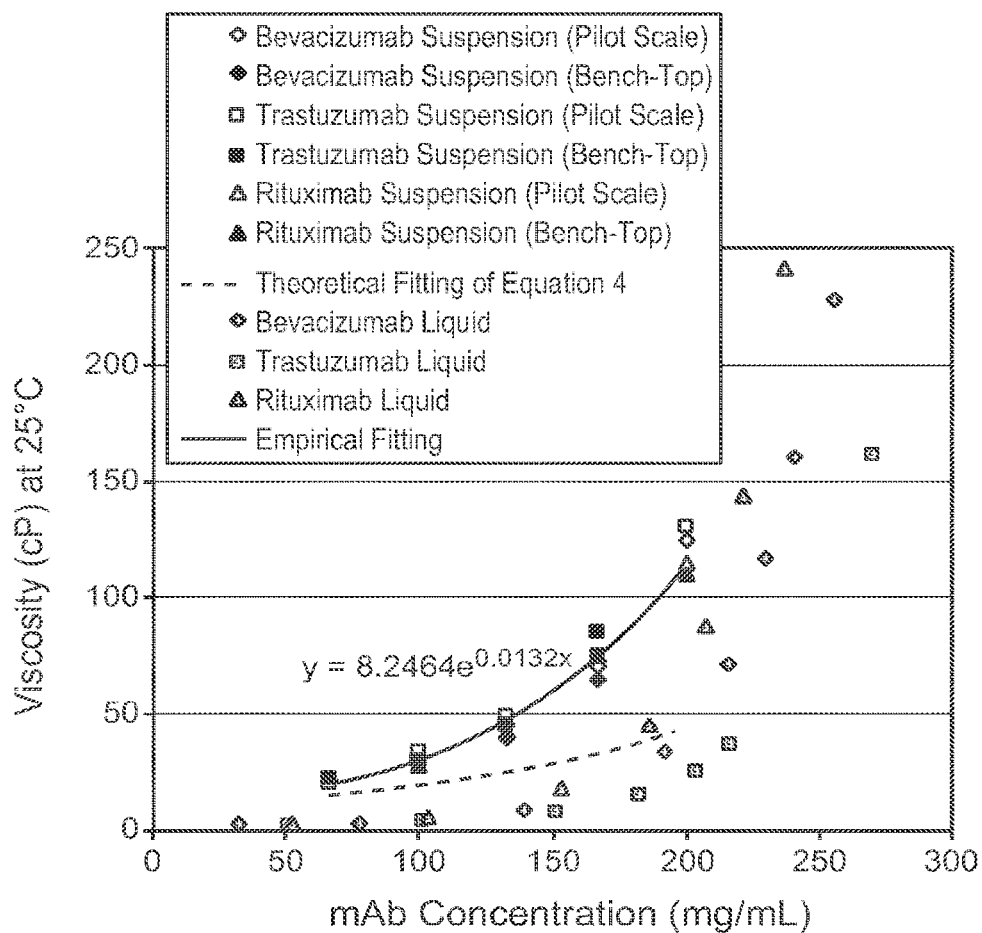
FIG. 2: The viscosity-powder concentration profiles for propylene glycol dicaprylate/dicaprate suspensions with three monoclonal antibody (mAb) powders spray dried with a pilot-scale or a bench-top spray dryer: bevacizumab by pilot-scale (◇), bevacizumab by bench-top (♦), trastuzumab by pilot-scale (□), trastuzumab by bench-top (■), rituximab by pilot-scale (Δ), rituximab by bench-top (▲), empirical fitting (solid line), and theoretical fitting from Equation 4 (dash line).

All antibodies dried by both bench-top and pilot-scale spray dryers (Table 2) were suspended in propylene glycol dicaprylate/dicaprate. Suspension viscosity was measured as a function of antibody concentration, and compared to the antibody liquid solutions (FIG. 2). Suspension viscosity for all antibodies was similar in the range of antibody concentration tested, suggesting that variations in antibody types and powder properties (particle size, morphology, and moisture content) had little effect on suspension viscosity. Suspension viscosity increased with increasing antibody concentration in an exponential manner, which can be expressed as:

$$\eta_{Miglyol\ 840}=8.24e^{0.0088(powder\ conc)} \quad \text{(Equation 3)}$$

Certainly, it is very different from the Einstein equation (Equation 2) which is primarily for dilute suspensions.

Equation 4, a modified version of Equation 2, took the interactions of more concentrated suspensions into consideration (Kunitz, M., J. *General Physiology* pages 715-725 (July 1926)), however, it still significantly underestimated the empirical data (see the dash line in FIG. 2).

$$\eta/\eta_o=(1+0.5\varphi)/(1-\varphi)^4 \quad \text{(Equation 4)}$$

It was interesting to find that suspension viscosity was actually higher than the viscosity of the corresponding antibody liquid solution at the same antibody concentration. No difference in suspension viscosity was observed among the antibodies, although the type of antibody did significantly affect liquid viscosity.

Surface Energies of Spray Dried Powders by IGC

Kanai and co-workers (Kanai et al., *J. Pharm. Sri.* 97:4219-4227 (2005)) found reversible self-association as the result of Fab-Fab interactions in their viscosity study tested with two antibodies made of the same construct with different amino acid sequences in the complementarity determining region (CDR) region in aqueous solutions. Such viscosity differences due to the antibody types in powder suspensions in non-aqueous vehicles were not observed (FIG. 2). This observation could be interpreted from the perspective of particle surface energy distribution in the powder suspension. Particle surface energy, the combination of polar and non-polar (dispersive) energy components, can dictate the level of interactions with suspension vehicles and particles. IGC is a common tool for surface energy measurement. The particle's dispersive surface energy using decane, nonane, octane and heptane as the probes, and also specific acid-base (polar) Gibbs free energy were measured using acetone, ethyl acetate, ethanol, and acetonitrile as the

TABLE 3

Structure, viscosity, and pharmaceutical application information of three model suspension vehicles tested in this study

| | Miglyol 840 | Ethyl Lactate | Benzyl Benzoate |
|---|---|---|---|
| Structure | [structure image] | [structure image] | [structure image] |
| Viscosity (cp) at 20° C. | 9 | 2 | 9 |
| Pharmaceutical Applications | Not currently approved for parenteral use, but some animal tox studies have been conducted for skin delivery | Used as flavor enhancer for oral dose medications. Not approved for parenteral use but acute toxity in mice by SC and IV are available | Used as a preservative in liquid dosage form for parenteral administration in quantities less than 10% | probes. Surface energy is a distribution in response to particle size distribution of the powder sample but only surface energies at the 50% values were reported in Table 4. The dispersive surface energy, $\gamma_{50}$, was in a narrow range of 36 to 38 mJ/m² for all three antibodies. The differences in specific acid-base Gibbs free energy, $\Delta G_{50}$, of these antibodies in response to the four acid-base probes were also in a narrow range of 8 to 13 mJ/m². The comparable surface energy distribution among the three antibody powders could explain similar particle-suspension vehicle and particle-particle interactions, leading to their comparable suspension viscosity in propylene glycol dicaprylate/dicaprate (FIG. 2).

TABLE 4

Dispersive surface energy ($\gamma_{50}$), specific acid-base Gibbs free energy ($\Delta G_{50}$), and heat of sorption of spray dried monoclonal antibody powders (all measured using IGC)

| Powder | Suspension Vehicles | $\gamma_{50}$ (mJ/m²) | $\Delta G_{50}$ (mJ/m²) | Heat of Sorption $\Delta H_{sorption}$ (KJ/mole) |
|---|---|---|---|---|
| Bevacizumab | Decane, nonane, octane and heptane | 37.5 | | |
| Trastuzumab | Decane, nonane, octane and heptane | 36.8 | | |
| Rituximab | Decane, nonane, octane and heptane | 38.3 | | |
| Bevacizumab | Acetone | | 8.4 | |
| | Ethyl acetate | | 6.2 | |
| | Ethanol | | 14.8 | |
| | Acetonitrile | | 12.9 | |
| Trastuzumab | Acetone | | 8.2 | |
| | Ethyl acetate | | 6.6 | |
| | Ethanol | | 14.5 | |
| | Acetonitrile | | 12.7 | |
| Rituximab | Acetone | | 8.4 | |
| | Ethyl acetate | | 7.3 | |
| | Ethanol | | 14.9 | |
| | Acetonitrile | | 12.8 | |
| Bevacizumab | Propylene glycol dicaprylate/dicaprate | | | 39.9 ± 0.5 |
| | Benzyl benzoate | | | 36.5 ± 0.7 |
| | Ethyl lactate | | | 51.5 ± 0.3 |
| Rituximab | Propylene glycol dicaprylate/dicaprate | | | 43.4 ± 0.5 |
| | Benzyl benzoate | | | 42.8 ± 0.6 |
| | Ethyl lactate | | | 58.5 ± 0.4 |

Injectability of Suspensions in Three Vehicles

Figure 3:
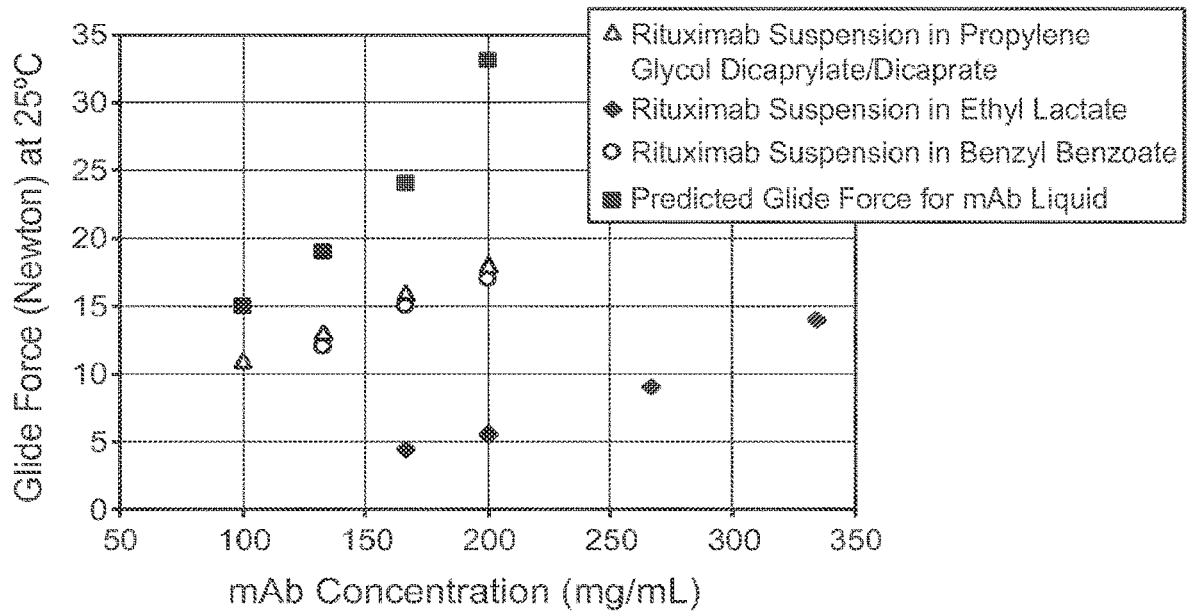
FIG. 3: The glide force-mAb concentration profiles for rituximab powder suspension in propylene glycol dicaprylate/dicaprate (Δ), ethyl lactate (◇), benzyl benzoate (○) and predicted glide force for mAb liquid solution extracted from FIG. 4 in Overcashier et al. *Am. Pharm Rev.* 9(6): 77-83 (2006) (■).

Injectability can be monitored by glide force measurement, which is a performance indicator more relevant than viscosity measurement. The glide force of the rituximab powder suspension in three vehicles was determined as a function of antibody concentration by injecting 1-mL suspension using a 1-mL long syringe through a 27-gauge TW staked needle in 10 seconds (FIG. 3). The glide force for all suspensions increased with antibody concentration, however, it was below 20 N even at 200 mg/mL antibody concentration despite the high viscosity (FIG. 2). The predicted glide force for the antibody liquid solutions extracted from FIG. 4 in Reference 3 was higher than the suspension glide force. The glide force in ethyl lactate suspension was lowest among the three suspension vehicles tested. The glide force of the ethyl lactate suspension at 333 mg antibody/mL was equivalent to that in the other two suspension vehicles at about half of the antibody concentration (167 mg/mL), which was still below the target threshold of 15 newton, even at high antibody concentration of 333 mg/mL. The reasons for the viscosity-glide force relationship discrepancy between the liquid solution and the suspension are not clear.

Effect of Suspension Vehicle on Suspension Viscosity

Figure 4:
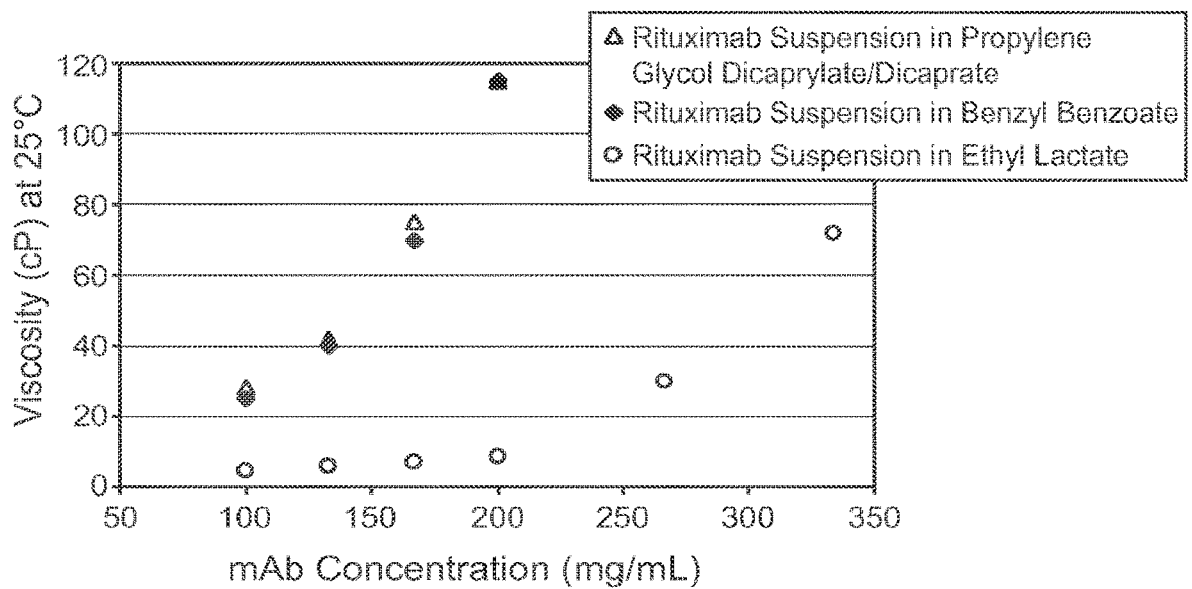
FIG. 4: The profiles of viscosity-mAb concentration for rituximab powder suspension in propylene glycol dicaprylate/dicaprate (Δ), in benzyl benzoate (◇), and in ethyl lactate (○).

Suspension viscosity was tested in three vehicles containing the spray dried rituximab powder (FIG. 4). The viscosity in ethyl lactate was the lowest among the three vehicles; the viscosity of the ethyl lactate suspension at 333 mg antibody/mL was equivalent to that of the suspension in propylene glycol dicaprylate/dicaprate and benzyl benzoate at about half of the antibody concentration (167 mg/mL).

Heat of Sorption by IGC and Particle Size

Heat of sorption ($\Delta H_{sorption}$) is a direct measure of the strength of the interactions between a solid and gas molecules adsorbed on the surface (Thielmann F., "Inverse gas chromatography: Characterization of alumina and related surfaces," In "*Encyclopedia of Surface and Colloid Science* Volume 4 (edit by P. Somasundaran) CRC Press. Boca Raton. FL., p 3009-3031 (2006); Thielmann and Butler, "Heat of sorption on microcrystalline cellulose by pulse inverse gas chromatography at infinite dilution," Surface Measurement Services Application Note 203 (http://www.thesorptionsolution.com/Information_Application_Notes_IGC.php#Aps) (2007)).

Figure 5:
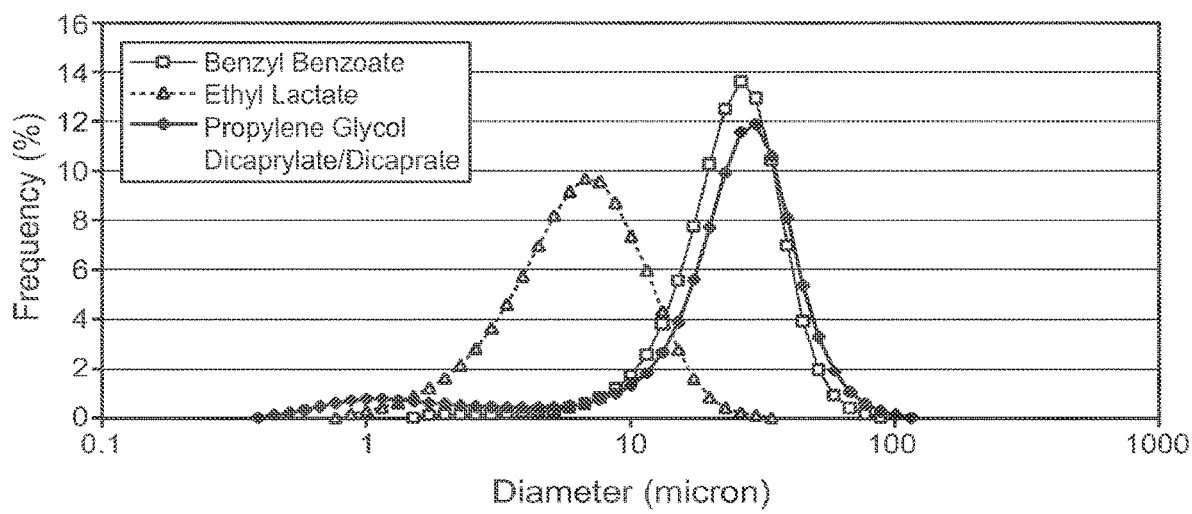
FIG. 5: Particle size distribution of rituximab suspensions in propylene glycol dicaprylate/dicaprate (◇), in benzyl benzoate (□), and in ethyl lactate (Δ).

The IGC method was employed to measure the heat of sorption between spray dried particles and the suspension vehicles (Table 4). For both bevacizumab and rituximab, ethyl lactate suspension had higher heat of sorption than the other two suspension vehicles. Particle size of the suspension particles was also compared among the three suspensions (FIG. 5). The peak particle size (highest percentage) was 28, 25, and 7 mm for propylene glycol dicaprylate/dicaprate, benzyl benzoate and ethyl lactate, respectively. Both heat of sorption and particle size data show that the higher heat of sorption in ethyl lactate suspensions indicated higher particle-suspension vehicle interaction than particle-particle interaction and that the degree of particle self-association in ethyl lactate was lower than that in propylene glycol dicaprylate/dicaprate or benzyl benzoate.

Suspension Physical Stability

Figure 6A:
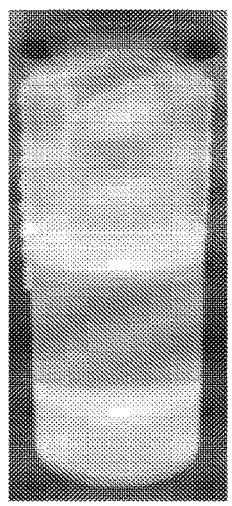
Figure 6B:
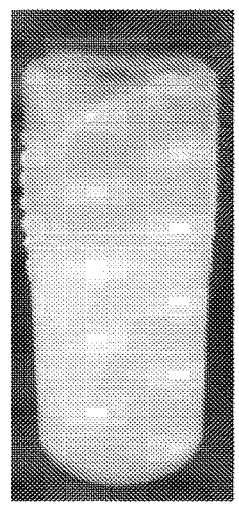
Figure 6C:
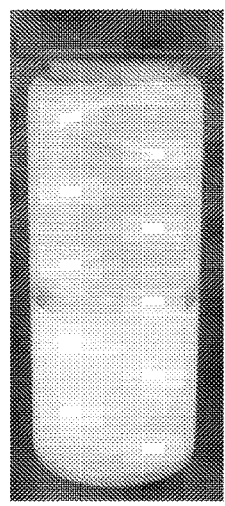

Despite low viscosity and glide force in the ethyl lactate suspension, it displayed a peculiar suspension physical stability as a function of time. The powder in the ethyl lactate suspension settled to the bottom and floated to the surface of the suspension after 1-day ambient storage (FIG. 6A). Homogeneity of the ethyl lactate suspension could be restored by vortexing (FIG. 6B). On the contrary, the suspension physical stability in propylene glycol dicaprylate/dicaprate was much more stable and remained well suspended over two weeks (FIG. 6C).

According to the particle sedimentation rate determined by Stoke's Law (Eq. 4 below), the particles in ethyl lactate would settle approximately 4.5 times faster than in propylene glycol dicaprylate/dicaprate, based on the density and viscosity of ethyl lactate and propylene glycol dicaprylate/dicaprate, 1.03 g/cm³ and 0.92 g/cm³, and 2 cP and 9 cP, respectively. Thus, Stoke's Law alone couldn't fully explain the observation of extremely fast settlement of particles in ethyl lactate as compared to propylene glycol dicaprylate/dicaprate, suggesting other mechanisms such as surface electrical charge (i.e., zeta potential) may play a role. However, the phenomenon of some of the particles floating to the top of ethyl lactate surface is difficult to explain because the density of the spray dried particles is higher than ethyl lactate.

$$s = d(\rho_s - \rho_l)g/(18\eta) \qquad \text{(Equation 5)}$$

where s is sedimentation rate, d diameter of the particle, $\rho_s$ the density of the particle, $\rho_l$ the density of the suspension vehicle, g acceleration due to gravity, and $\eta$ the viscosity of the suspension vehicle.

Suspension Vehicle Mixture to Improve Suspension Performance

Figure 7A:
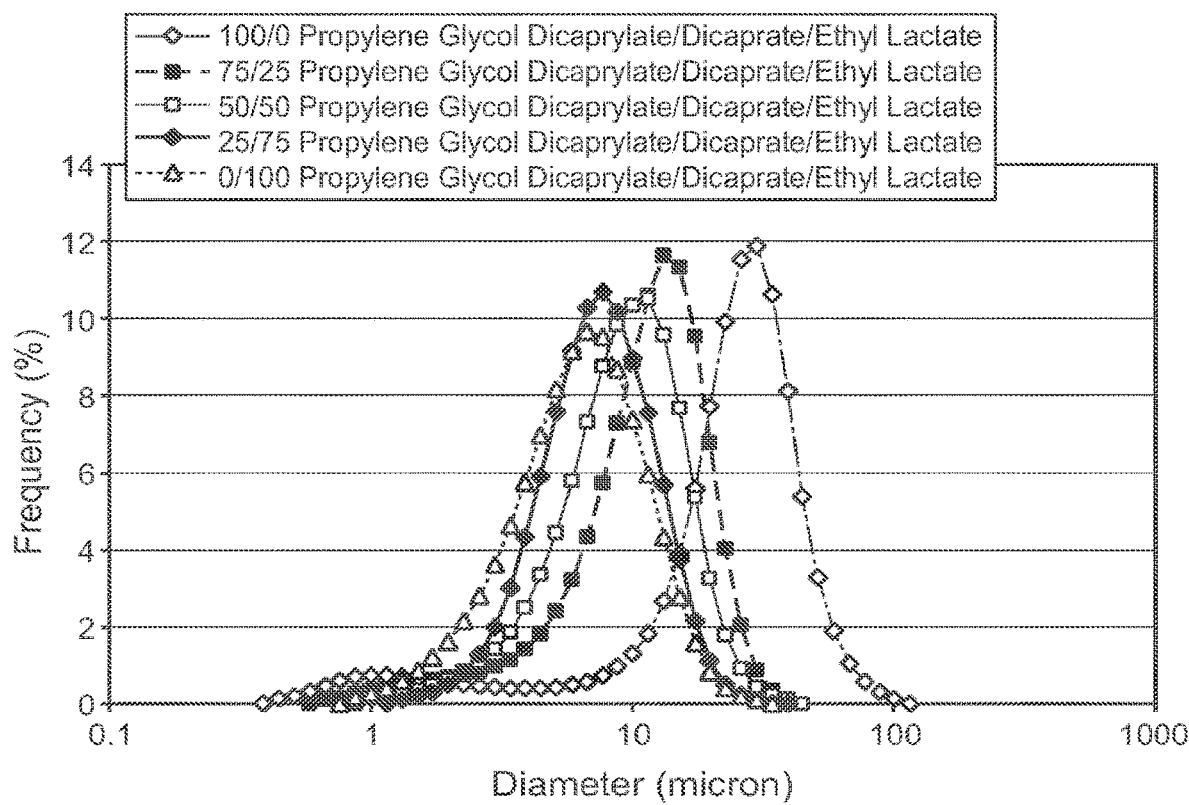
Figure 7B:
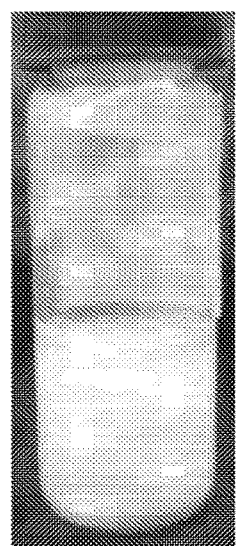

The mixtures of ethyl lactate and propylene glycol dicaprylate/dicaprate were used as suspension vehicles for testing rituximab suspension physical stability. Particle size was determined for these mixture suspensions (FIG. 7A). The particle size decreased with decreasing propylene glycol dicaprylate/dicaprate contribution in the mixture where the peak particle size was 28, 13, 11, 8 and 7 µm for propylene glycol dicaprylate/dicaprate:ethyl lactate mixture at 100:0, 75:25, 50:50, 25:75, and 0:100, respectively. From the suspension physical stability perspective, the poor suspension stability of ethyl lactate was improved by mixing with a small amount of propylene glycol dicaprylate/dicaprate as demonstrated in FIG. 7B where homogeneous suspension was maintained for rituximab powder in 25:75 propylene glycol dicaprylate/dicaprate:ethyl lactate mixture after 2-week ambient storage. It was demonstrated that overall suspension performance can be improved using a suspension vehicle mixture.

CONCLUSIONS

These examples demonstrated that the non-aqueous powder suspension approach was feasible for high monoclonal antibody concentration SC administration. Dry powder preparation by spray-drying was scalable using the high efficiency spray-drying process. The most important parameter for overall suspension performance was determined to be the type of suspension vehicle. Powder suspension in ethyl lactate displayed excellent suspension injectability with a low glide force of <15 N via a 27-gauge TW staked needle for antibody concentration as high as 333 mg/mL (total powder concentration of 500 mg/mL). Without being bound by any one theory, low viscosity and injectability could be attributed to strong particle-suspension vehicle interaction that prevents particle-particle agglomeration into larger particle size in the suspension. However, this mechanism did not support physical suspension stability. Dry antibody particles had a higher tendency to settle out in the ethyl lactate suspension than in propylene glycol dicaprylate/dicaprate. The approach of using suspension vehicle mixture proved to be effective in improving overall suspension performance.

What is claimed is:

1. A suspension formulation comprising a spray dried monoclonal antibody at a concentration of about 200 mg/mL to about 500 mg/mL suspended in a non-aqueous suspension vehicle, wherein the monoclonal antibody is a full length IgG1 antibody, the viscosity of the suspension vehicle is less than about 20 centipoise at about 25° C., and the suspension vehicle is ethyl lactate.

2. The formulation of claim 1 wherein the injection glide force of the formulation is about 20 newton or less.

3. The formulation of claim 1 wherein the average particle size in the formulation is from about 2 microns to about 30 microns or from about 2 microns to about 10 microns.

4. The formulation of claim 1 wherein the antibody concentration in the formulation is from about 200 mg/mL to about 350 mg/mL.

5. The formulation of claim 1 further comprising a saccharide.

6. The formulation of claim 5 wherein the saccharide is trehalose or sucrose.

7. The formulation of claim 5 wherein the molar ratio of saccharide: monoclonal antibody is from about 50 to about 400:1 or from about 100 to about 250:1.

8. The formulation of claim 1 further comprising a surfactant.

9. The formulation of claim 8 wherein the surfactant is polysorbate 20 or polysorbate 80.

10. The formulation of claim 1 which is suitable for subcutaneous administration.

11. The formulation of claim 1 wherein the monoclonal antibody is a human IgG1.

12. The formulation of claim 1 wherein the monoclonal antibody is a chimeric, humanized, or human antibody.

13. The formulation of claim 1 wherein the monoclonal antibody binds an antigen selected from the group consisting of: CD20, HER2, VEGF, IL6R, beta7, Abeta, HER3, EGFR, and the small extracellular segment on IgE (M1').

14. A subcutaneous administration device with the formulation of claim 1 therein.

15. A method of making a suspension formulation comprising suspending a spray dried monoclonal antibody in a non-aqueous suspension vehicle with a viscosity less than about 20 centipoise at about 25° C., wherein the monoclonal antibody concentration in the suspension formulation is about 200 mg/mL to about 500 mg/mL and wherein the suspension vehicle is ethyl lactate.

16. A method of making an article of manufacture comprising filling a subcutaneous administration device with the formulation of claim 1.

17. A suspension formulation comprising a spray dried full length human IgG1 monoclonal antibody at a concentration from about 200 mg/mL to about 400 mg/mL suspended in a non-aqueous suspension vehicle with a viscosity less than about 20 centipoise, wherein the suspension vehicle is ethyl lactate, and wherein the formulation has an average particle size from about 2 microns to about 10 microns, and injection glide force less than about 15 newton.

18. The formulation of claim 12, wherein the monoclonal antibody is rituximab.

19. The formulation of claim 12, wherein the monoclonal antibody is trastuzumab.

20. The formulation of claim 12, wherein the monoclonal antibody is bevacizumab.

* * * * *

SEQUENCE LISTING

```
<160> NUMBER OF SEQ ID NOS: 30

<210> SEQ ID NO 1
<211> LENGTH: 451
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
            195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Synthetic Construct

<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95
```

```
Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 3
<211> LENGTH: 121
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala
            115                 120

<210> SEQ ID NO 4
<211> LENGTH: 106
<212> TYPE: PRT
<213> ORGANISM: Artificial Sequence
<220> FEATURE:
<223> OTHER INFORMATION: Synthetic Construct

<400> SEQUENCE: 4

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60
```

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Ser Tyr Asn Met His
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct

<400> SEQUENCE: 6

Ala Ile Tyr Pro Gly Asn Gly Asp Thr Ser Tyr Asn Gln Lys Phe Lys
1               5                   10                  15

Gly

<210> SEQ ID NO 7
<211> LENGTH: 12
<212> TYPE: PRT
<213> ORGANISM: Artificial Sequence
<220> FEATURE:
<223> OTHER INFORMATION: Synthetic Construct

<400> SEQUENCE: 7

Ser Thr Tyr Tyr Gly Gly Asp Trp Tyr Phe Asn Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Arg Ala Ser Ser Ser Val Ser Tyr Ile His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Ala Thr Ser Asn Leu Ala Ser
1               5

<210> SEQ ID NO 10

<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Gln Gln Trp Thr Ser Asn Pro Pro Thr
1               5

<210> SEQ ID NO 11
<211> LENGTH: 453
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu

```
            305                 310                 315                 320
Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Met Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
            450

<210> SEQ ID NO 12
<211> LENGTH: 214
<212> TYPE: PRT
<213> ORGANISM: Artificial Sequence
<220> FEATURE:
<223> OTHER INFORMATION: Synthetic Construct

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

-continued

```
<210> SEQ ID NO 13
<211> LENGTH: 123
<212> TYPE: PRT
<213> ORGANISM: Artificial Sequence
<220> FEATURE:
<223> OTHER INFORMATION: Synthetic Construct

<400> SEQUENCE: 13
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

```
<210> SEQ ID NO 14
<211> LENGTH: 108
<212> TYPE: PRT
<213> ORGANISM: Artificial Sequence
<220> FEATURE:
<223> OTHER INFORMATION: Synthetic Construct

<400> SEQUENCE: 14
```

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

```
<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15
```

Gly Tyr Thr Phe Thr Asn Tyr Gly Met Asn
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Trp Ile Asn Thr Tyr Thr Gly Glu Pro Thr Tyr Ala Ala Asp Phe Lys
1               5                   10                  15

Arg

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct

<400> SEQUENCE: 17

Pro His Tyr Tyr Gly Ser Ser His Trp Tyr Phe Asp Val
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Ser Ala Ser Gln Asp Ile Ser Asn Tyr Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Phe Thr Ser Ser Leu His Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Gln Gln Tyr Ser Thr Val Pro Trp Thr
1               5

<210> SEQ ID NO 21
<211> LENGTH: 449
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Val Glu Ser Gly Gly Gly Leu Val Gln Pro Gly Gly

-continued

```
1               5                   10                  15
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

Glu Ala Leu His Asn His Tyr Thr Gln Lys Ser Leu Ser Leu Ser Pro
        435                 440                 445
Gly

<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 120
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 24
<211> LENGTH: 108
<212> TYPE: PRT
<213> ORGANISM: Artificial Sequence
<220> FEATURE:
<223> OTHER INFORMATION: Synthetic Construct

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Gly Phe Asn Ile Lys Asp Thr Tyr Ile His
1               5                   10

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Arg Ile Tyr Pro Thr Asn Gly Tyr Thr Arg Tyr Ala Asp Ser Val Lys
1               5                   10                  15

Gly

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

```
<400> SEQUENCE: 27

Trp Gly Gly Asp Gly Phe Tyr Ala Met Asp Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Arg Ala Ser Gln Asp Val Asn Thr Ala Val Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Ser Ala Ser Phe Leu Tyr Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Construct

<400> SEQUENCE: 30

Gln Gln His Tyr Thr Thr Pro Pro Thr
1               5
```